(12) United States Patent
Brahme et al.

(10) Patent No.: US 7,400,434 B2
(45) Date of Patent: Jul. 15, 2008

(54) RADIATION MODULATOR

(75) Inventors: Anders Brahme, Danderyd (SE);
Pontus Nelldal, Stockholm (SE);
Andras Kerek, Danderyd (SE); Bo Haggstrom, Stockholm (SE)

(73) Assignee: C-Rad Innovation AB, Uppsala (SE)

( * ) Notice: Subject to any disclaimer, the term of this patent is extended or adjusted under 35 U.S.C. 154(b) by 226 days.

(21) Appl. No.: 11/204,054

(22) Filed: Aug. 16, 2005

(65) Prior Publication Data
US 2007/0040127 A1 Feb. 22, 2007

(51) Int. Cl.
*G02B 26/00* (2006.01)
*A61N 5/10* (2006.01)

(52) U.S. Cl. .......................... 359/237; 378/65
(58) Field of Classification Search ................. 359/237; 378/150–151
See application file for complete search history.

(56) References Cited

U.S. PATENT DOCUMENTS 5,596,619 A * 1/1997 Carol .......................... 378/65
5,802,136 A * 9/1998 Carol .......................... 378/65

OTHER PUBLICATIONS

Xu et al., "Reshapable physical modulator for intensity modulated radiation therapy", Am. Assoc. Phys. Med., vol. 29, No. 10, Oct. 2002, pp. 2222-2229.
T. Watanabe and H. Kuwano, "A microwave matrix using piezoelectric actuators", Microsystems Technologies, 1997, pp. 107-111.

* cited by examiner

*Primary Examiner*—Jordan M. Schwartz
*Assistant Examiner*—James C Jones
(74) *Attorney, Agent, or Firm*—Young & Thompson

(57) ABSTRACT

A radiation beam modulator (1; 500; 600) that can be employed for modulating a radiation beam (60) in a radiation system. The modulator (1; 500; 600) comprises a bath (590; 690) containing a radiation attenuating fluid (520; 620) and multiple low radiation attenuating bars (570; 670) immersed in the fluid (520; 620) to form an array of multiple columns (525; 625). A height adjuster (530; 630) is arranged for adjusting a respective level of immersion of the bars (570; 670) in the fluid (520; 620) thereby to adjust the heights of the fluid columns (525; 625) such that the columns (525; 625) collectively form a radiation beam modulating profile.

16 Claims, 20 Drawing Sheets

RADIATION MODULATOR

TECHNICAL FIELD

The present invention generally relates to radiation beam modulators, and generally to adjustable physical modulators for providing modulated radiation beams.

BACKGROUND

During the past decades there have been considerable developments within the fields of radiation therapy and tumor diagnosis. The performance of external beam radiation therapy accelerators, brachytherapy and other specialized radiation therapy equipment has improved rapidly. Significant developments have taken place in the quality and adaptability of the therapeutic radiation beams including new targets and filters, improved accelerators, increased flexibility in beam-shaping through new applicators, collimators, scanning systems and beam compensation techniques. Also improved dosimetric and geometric treatment verification methods have been introduced. Furthermore, advanced treatment planning systems capable of biological optimization of the intensity distribution of the delivered beams are now being available.

Intensity modulated radiation therapy (IMRT) is a fairly new method in which arbitrary dose distribution can be achieved in the target volume by modulating the intensity profiles of the incident therapeutic beams. Unlike conventional thereby employing uniform beams, IMRT can deliver almost arbitrarily shaped dose distributions that conform to the target volume, i.e. tumor volume, while sparing neighboring organs at risk and healthy tissues.

Various techniques for shaping intensity modulated beams (IMBs) have been developed, which typically can be categorized into static and dynamic fluence delivery techniques, respectively. In the static fluence techniques, the individual IMB is a result of a fixed intensity modulation by a static filter or similar structure to treat the target volume, which sometimes is called a step and shoot technique. In the dynamic fluence delivery technique, the target is encompassed by a continuously varied intensity profile.

The most common clinical fluence modulation technique for today is usage of multileaf collimators (MLCs). In this technique, the beam is collimated by multiple pairs of opposite tungsten leafs positioned perpendicular to the beam direction. The MLC is ideal for irregular static fields, but is marred by drawbacks in dynamic applications due to the increased treatment times and constraints on leaf position and mechanical limits in leaf velocity and acceleration. Helical tomotherapy is a special case of dynamic MLC where each leaf has only two positions, in or out. This tomotherapy technique resembles computerized tomography (CT) since the radiation source is rotated around the patient while the patient is moved axially through the field. A major drawback of dynamic MLC and the tomotherapy is lengthened total treatment time.

Intensity modulation can also be achieved by scanned beam therapy, in which a narrow, often Gaussian-shaped beam is scanned over the target. This modality has, so far, had somewhat restricted clinical use due to the increased cost of the required current systems. Furthermore, the beam resolution is limited for low energy electrons and photons. However, it is the state of the art technique for high energy electrons and photons as well as for light ions.

Static fluence modulation techniques for IMRT include usage of physical modulators, in which the whole target is encompassed simultaneously with a predetermined IMB profile. The IMB ca be achieved by intercepting the beam with a metal block of a thickness profile corresponding to the desired transmission profile. The simultaneous whole-filed irradiation results in higher monitor unit efficiency and less whole-body dose compared to sequential delivery of the dose segments. However, since traditional physical modulators require manual fabrication of different block shapes for each beam and manual exchange of these different blocks between beams, fixed physical modulators have to this date had limited clinical implementation.

Efforts have therefore been made ting to develop a more flexible physical modulator. A technique in which a machine automatically arranges metal cubes of two densities into certain patterns in order to provide a desired intensity modulator profile have been developed. Although this allows a more flexible modulator design, the total time of modulator profile exchange is still too large to be practically useful. In addition, the solid metal blocks inevitably imply restrictions.

Xu et al. [1] have presented a re-shapable modulator in which a mixture of tungsten powder, paraffin and silicon binder is shaped to a desired intensity modulator profile by a set of pistons. Still, the shaping is done outside the beam and therefore the modulator has no dynamic capabilities. In addition, a re-shaping of the modulator first requires shaping to uniform thickness before the target thickness distribution can be obtained, which prolongs the total re-shaping time The modulator presented by Xu et al., further has stability problems, implying that the shaped attenuating material may unintentionally deform during radiation therapy, especially when the modulator is in a non-horizontal position and/or is exposed to forces caused by rotation of the radiation gantry and the modulator.

Mark Carol [2] discloses an apparatus for conformal radiation therapy with a radiation beam having a pre-determined constant beam intensity that is spatially modulated across the tumor volume. The apparatus includes a housing having a plurality of compartments extending from the top to the bottom of the housing. Each such compartment has an inflatable balloon and is in contact with a pressurized reservoir containing mercury. When a particular balloon is deflated, mercury is pushed from the reservoir into the compartment associated with the balloon. Correspondingly, when a balloon is inflated, mercury is pushed from the associated compartment into the reservoir. The beam modulation is obtained by varying the amount of time each compartment is empty or fined with mercury.

SUMMARY

The present invention overcomes these and other drawbacks of the prior art arrangements.

It is a general object of the present invention to provide an adjustable radiation modulator.

It is another object of the invention to provide a radiation modulator that can be adjusted without first removing the modulator from its operation position.

It is a farther object of the invention to provide a radiation modulator for which the thickness distribution profile can have any modulating thickness between a maximum thickness and a minimum thickness.

It is a particular object of the present invention to provide a radiation modulator technique that can be used in intensity modulation for any neutral particle radiation type, such as photons neutrons, pions ($\pi_o$) etc., and energy or range modulation for charged particles like electrons and light ions.

These and other objects are met by the invention as defined by the accompanying patent claims.

Briefly, the present invention involves a radiation beam modulator having a modulating profile that can be dynamically adjusted to conform to a desired transmission profile for a given target volume and the location of organs at risk.

The modulator utilizes a fluid as modulating material and includes an array of multiple columns of this modulating fluid. A height adjuster is provided in the modulator for adjusting the heights of the multiple fluid columns. The so-adjusted columns will then collectively form a radiation beam modulating profile having the desired thickness distribution and modulating profile. A radiation beam passing through the modulating profile of the fluid columns will then become modulated, resulting in a modulated radiation beam.

In a preferred embodiment of the invention, the height adjuster is adapted for individually adjusting the heights of the multiple fluid columns in real time. In another embodiment, the heights of groups of fluid columns can be adjusted even though an individual column height adjustment is not possible.

The radiation modulating fluid is preferably a radiation attenuating fluid that is in liquid form at the operation temperature of the modulator. Preferred examples include mercury and liquid forms of Rose's or Wood's metal.

Different types of beam modulation can be obtained depending on the type of input beam and the properties of the radiation modulating fluid. Thus, the modulator of the invention can be employed for intensity modulating a photon beam or other neutral particle beam, for range or energy modulating a charged particle beam or luminosity modulation of a light beam.

In a first embodiment of the present invention, the modulator includes a bundle of divergent closely packed capillaries and a system for regulating the level of the radiation modulating fluid in these capillaries. The capillaries preferably have a hexagonal cross-section and the cross-section of their inner channels is preferably quasi-hexagonal in order to minimize the capillary wall thickness and the non-modulating area of the modulator. A first (entrance) end of the capillaries is in fluid contact with one or more fluid reservoirs from which and into which the radiation attenuating fluid can be directed. A second opposite end of the capillaries is preferably in fluid contact with one or more reservoirs containing an antagonizing fluid or gas having low radiation modulating/attenuating capability. As a consequence, the lower portion of the capillaries is preferably filled with the radiation modulating fluid and the antagonizing fluid flows thereon and occupies the upper remaining part of the capillaries.

The height adjuster can be implemented in the form of (micro) valves, fluid pressurizers and/or pumps that act on the radiation attenuating fluid and the antagonizing fluid or gas. In order to increase the height of a given fluid column in a capillary, radiation attenuating fluid is brought from the fluid reservoir into the first end of the capillary. Simultaneously, antagonizing fluid will flow out from the second end of the capillary and into the antagonizing reservoir. When decreasing a column height, the portion of antagonizing fluid in the capillary is increased at the cost of the amount of radiation attenuating fluid.

The antagonizing fluid and the height adjusting system furthermore actively maintains the adjusted column heights between adjustment occasions, thereby preventing unintentionally changes in the level of radiation attenuating fluid in the capillaries, which would result in a departure from the desired modulating profile in the target volume.

A second embodiment of the modulator utilizes a bath containing the radiation modulating fluid. Multiple low radiation modulating/attenuating bars are immersed in this fluid bath. The level of immersion of a given bar defines the height of the column of radiation modulating fluid positioned beneath the bar. The height adjuster is then configured for immersing the bars further into the fluid or retracting the bars slightly until the correct thickness distribution and modulating profile is obtained.

The bars preferably have a honeycomb-like hexagonal cross-section in order to enable the tightest packing thereof for a given number of bars and prevent any fluid leakage between adjacent bars.

The height adjuster can consist of a system of wire motors that drives wire loops connected to the respective ends of the bars. By then rotating the loops clockwise or counter-clockwise the bars will be lowered into or retracted from the fluid.

In an alternative solution, the multiple bars have a respective blind bore or blind hole. The bar further has a nut arranged in connection with the blind bore. At the top of the fluid bath is one or more low radiation attenuating plates arranged similar to a lock on a container. Multiple screws are attached to and fixed by the plates, through their screw heads so that the screws cannot move vertically but still be rotated. Each such screw runs in a respective blind bore of a bar through the nut of the bar.

The tight packing or squeezing together of the bars will prevent the bars from rotate. Thus, since a bar is kept in place between its neighboring bars, the bar can move vertically (immerse into or retract from the fluid) but not rotate. This means that when the screw associated with a particular bar is rotated or screwed, this rotating motion will cause the bar to move upwards towards the screw head or downwards away from the screw head and the radiation source. As a consequence, the level of immersion of a bar in the radiation attenuating fluid and, thus, the height of the fluid column directly below the bar, can be adjusted by rotating the screw.

In this embodiment of the modulator, the height adjuster thus includes a screw driver and preferably a set of multiple screw drivers. The screw driver set could be arranged in a similar array or matrix as the bar core, implying that there is one screw driver for each screw and bar. However, in embodiments with rather larger modulator cores, the number of screw drivers can be less than the number of screws and bars. In such a case, the screw drivers can (step-by-step) move between the screws and individually setting the desired bar immersion of the bars by rotating the screw head associated with the bar clockwise or counter-clockwise (or not at all if the bar already has the correct modulation and immersion level).

The invention offers the following advantages:

Provides a simple and inexpensive real-time adjustable and re-shapable radiation modulator, Modulating profile can be adjusted in-place and in a short period of time;

Enables a high resolution of the modulated radiation beam;

Enables real-time dynamic adjustment that can cope with dynamic capabilities such as compensation for organ motions during operation and multiple beam portions;

Has large modulation range since the thickness distribution profile can have any modulation thickness between a maximum and minimum thickness;

The modulator has high conformal capabilities that can be adjusted to vastly different target volumes;

Can be operated in a radiation system without any flattening filter;

Simultaneous IMB radiation of the whole target volume is possible for a radiation beam modulated according to the present invention, which results in a significantly shorter treatment time and higher monitor unit efficiency and smaller whole-body leakage dose; and An intensity modulation range of at least 100-1% is obtainable.

These and other advantages offered by the present invention will be appreciated upon reading of the below description of the embodiments of the invention.

SHORT DESCRIPTION OF THE DRAWINGS

The invention together with further objects and advantages thereof, may best be understood by making reference to the following description taken together with the accompanying drawings, in which.

Figure 1:
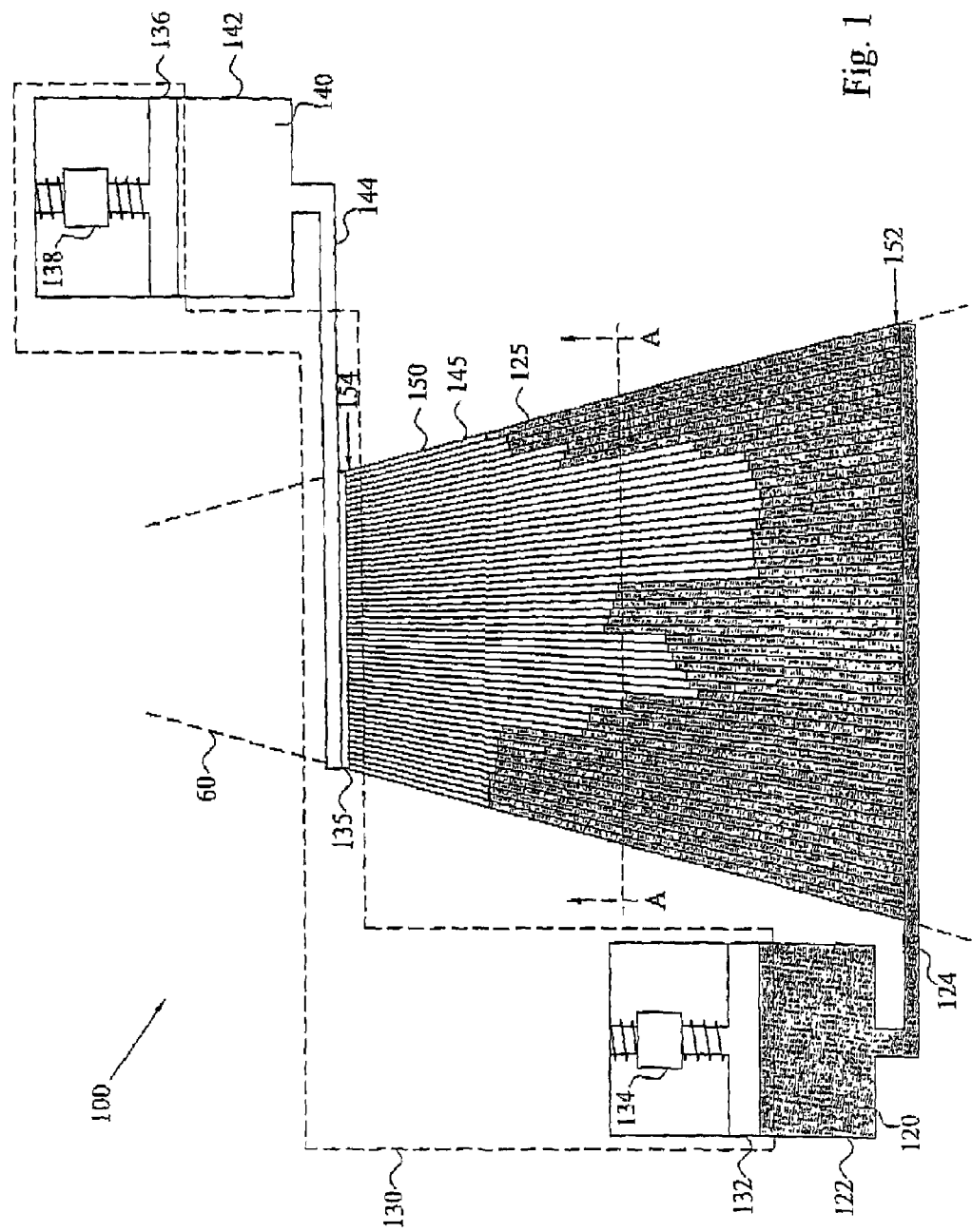
FIG. 1 illustrates a first embodiment of a radiation beam modulator according to the present invention.
Figure 3:
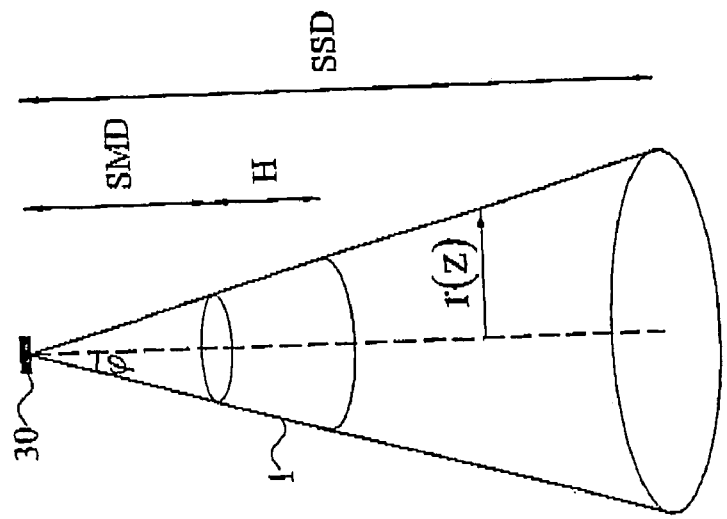
Figure 4A:
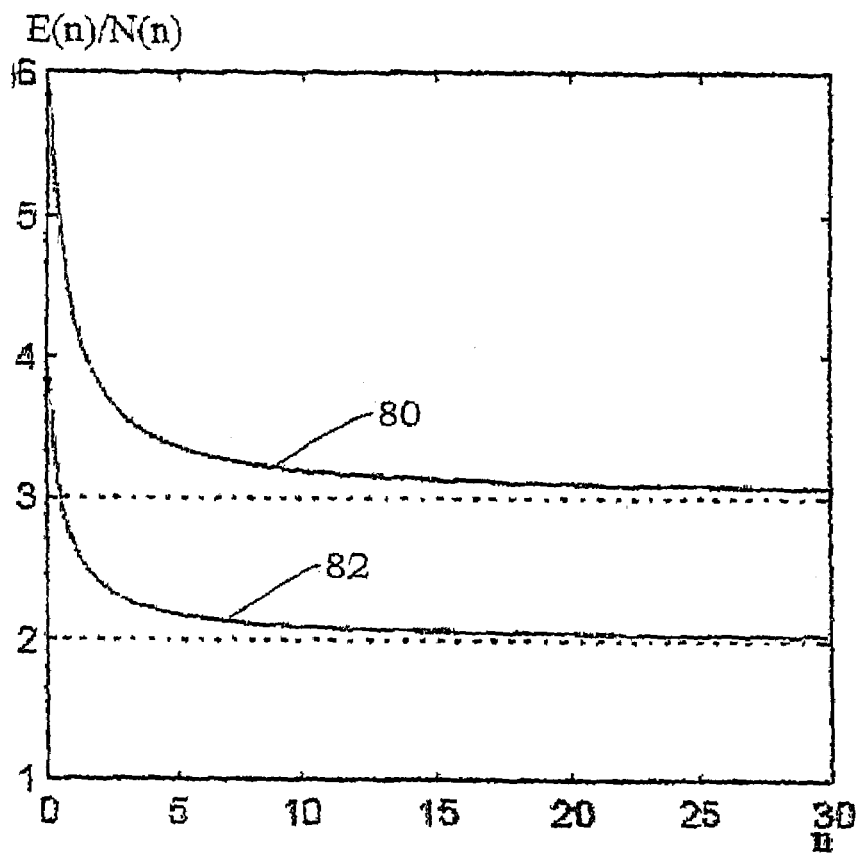
Figure 4B:
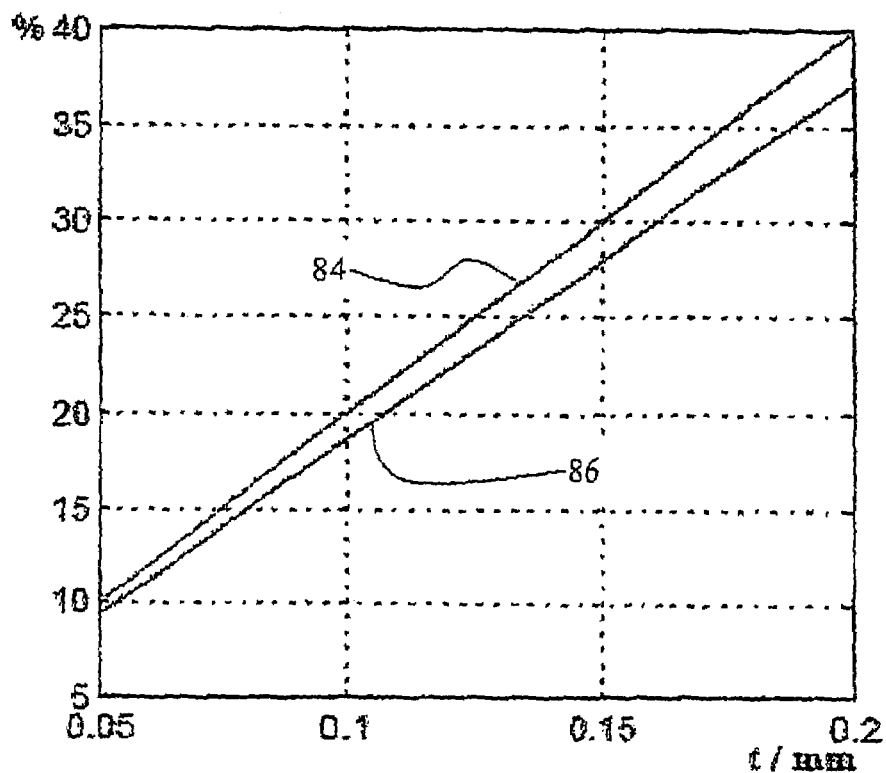
Figure 5A:
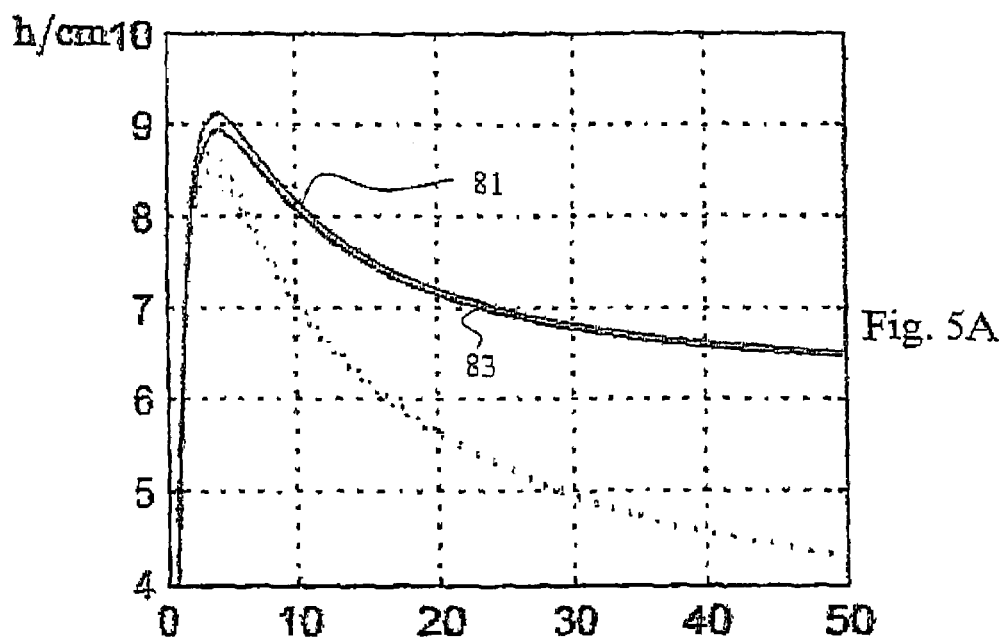
Figure 5B:
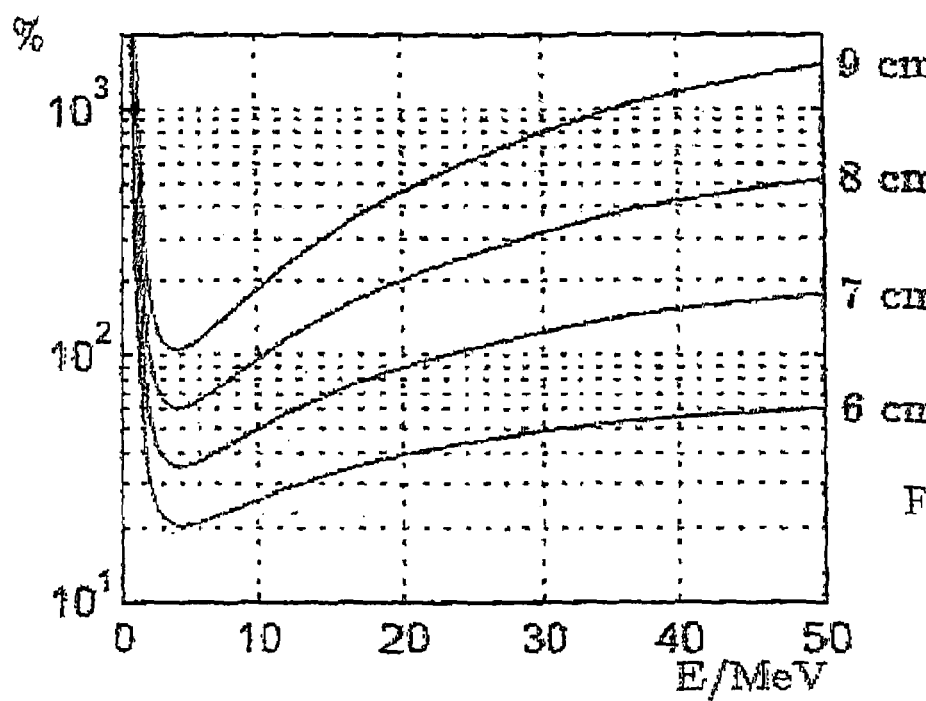
Figure 6:
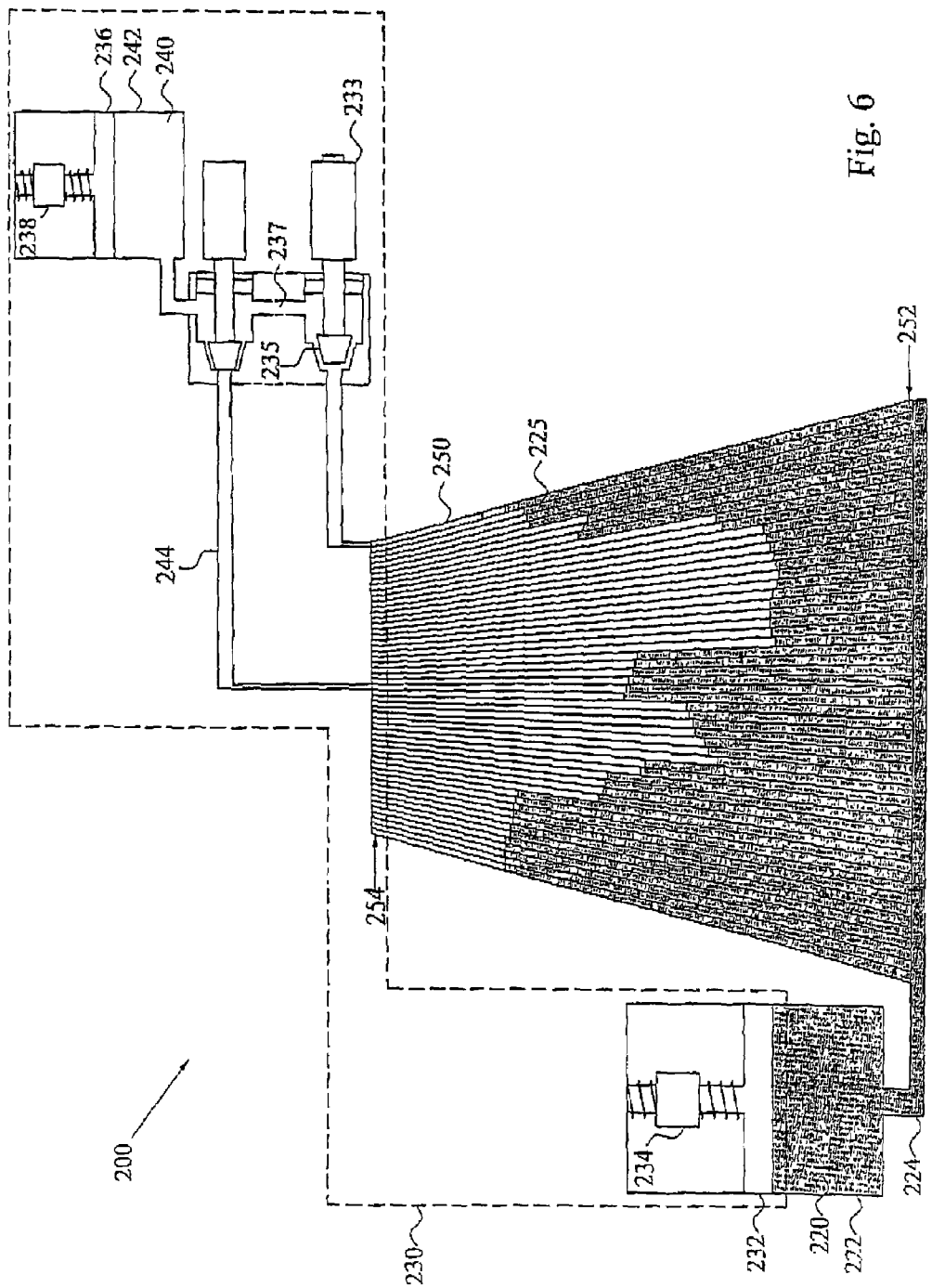
Figure 7:
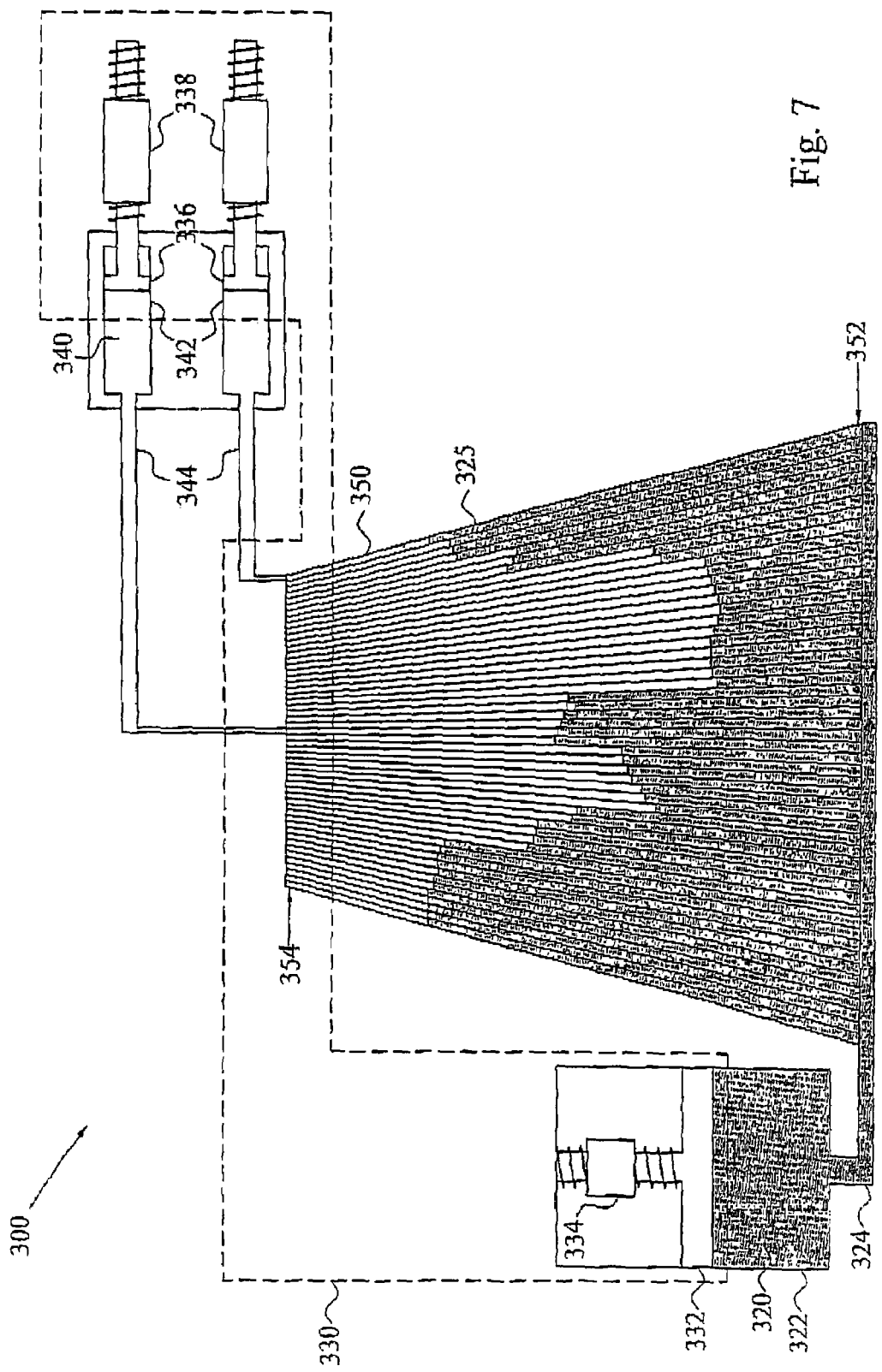
Figure 8:
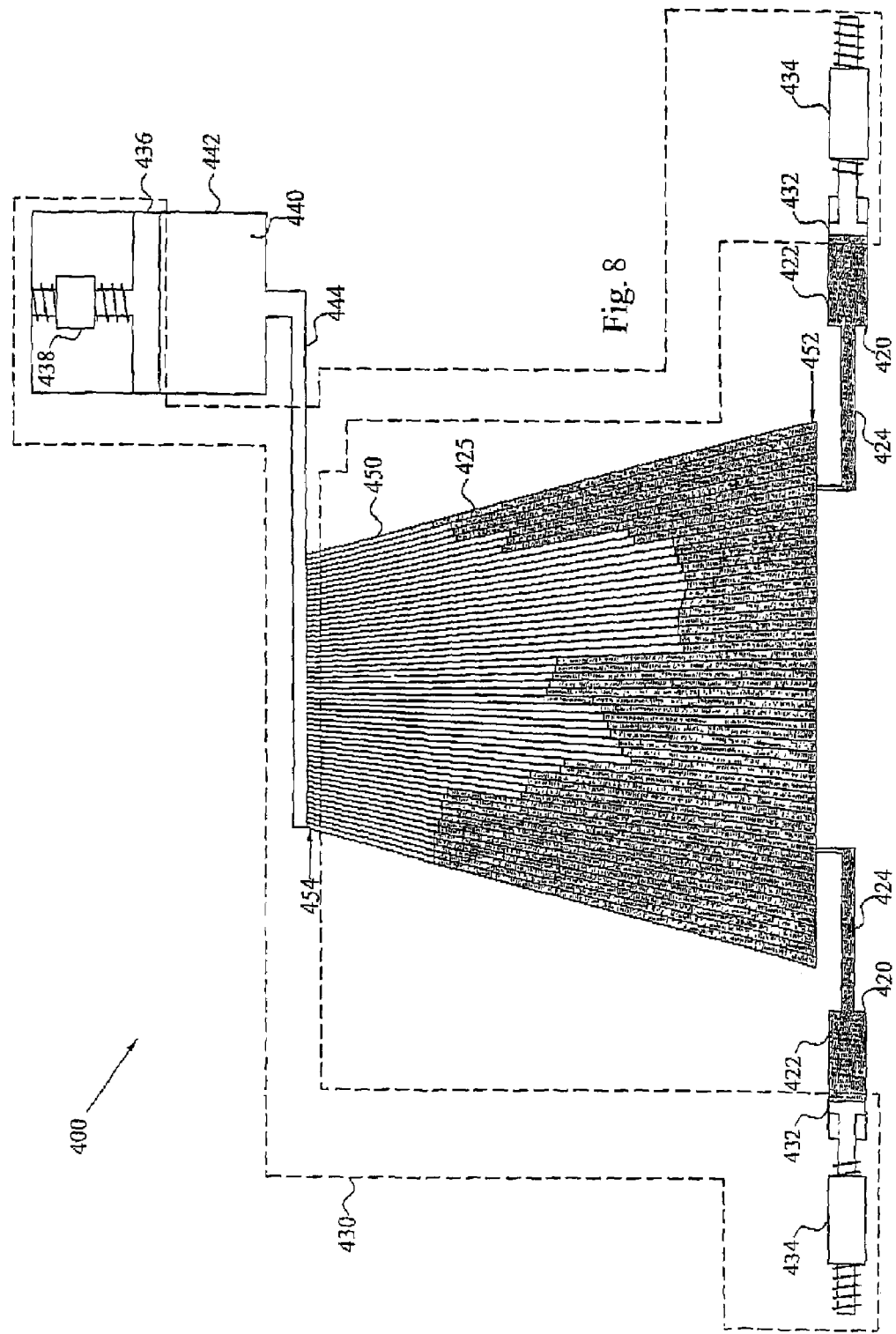
Figure 9:
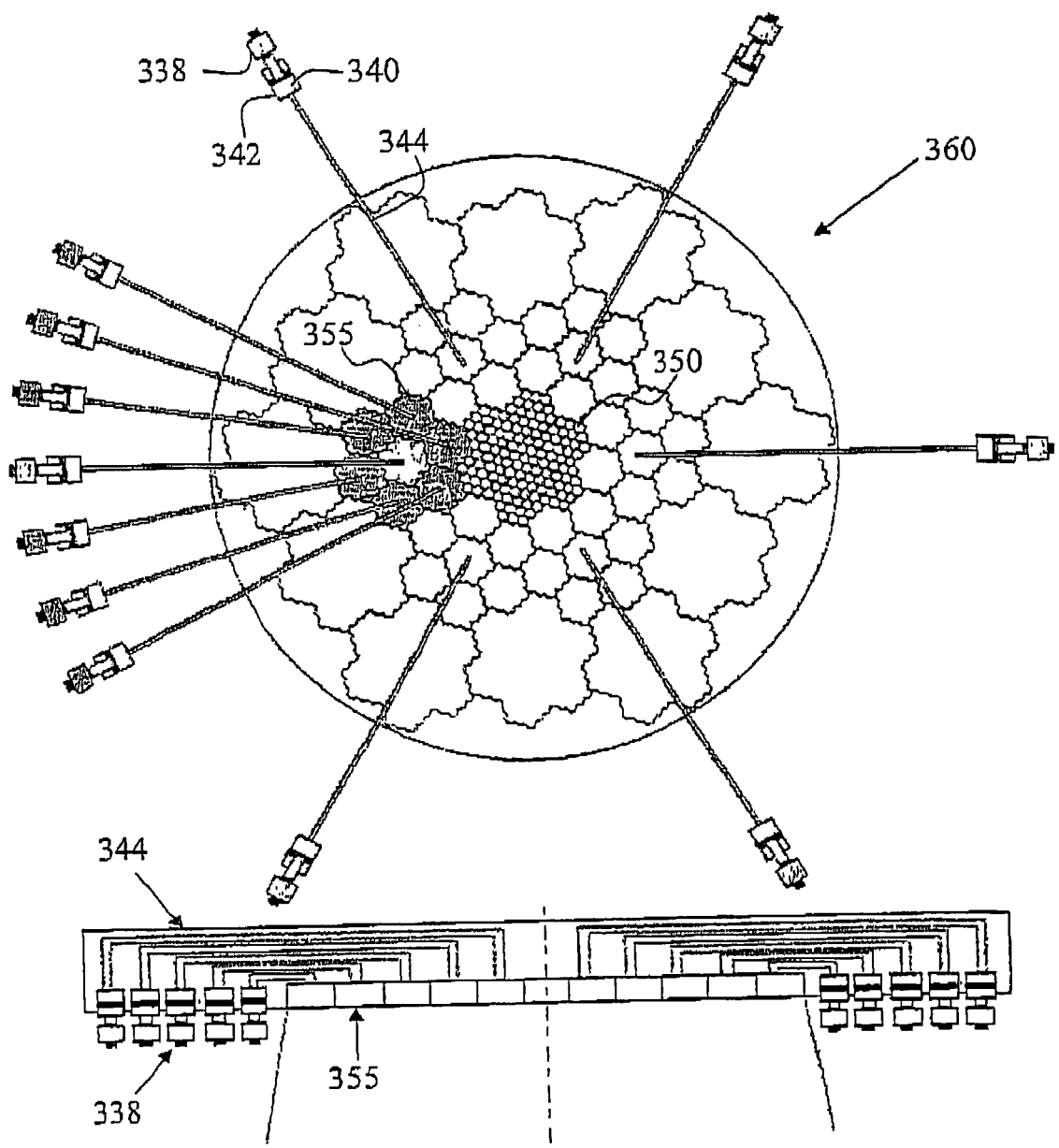
Figure 10:
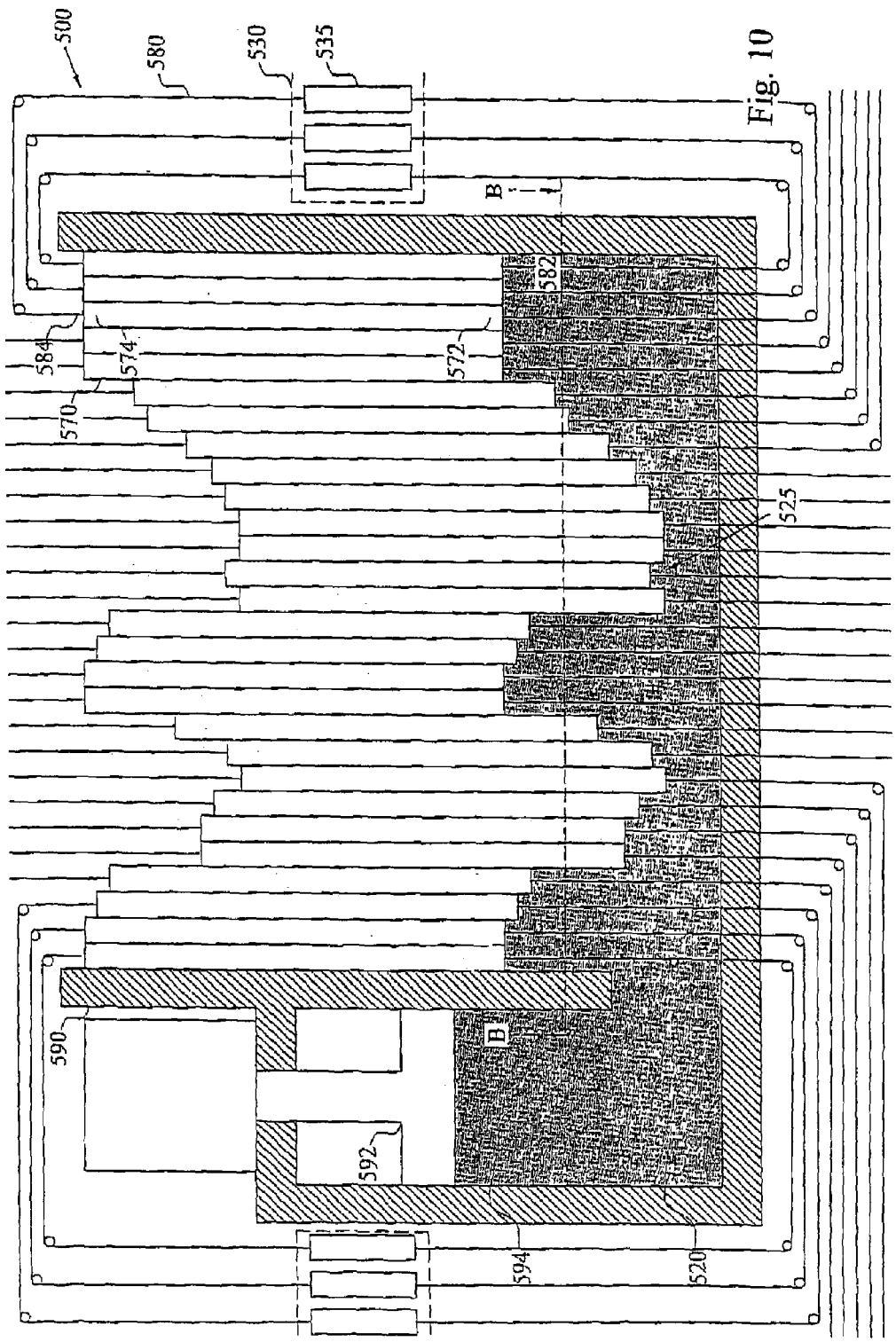
Figure 11:
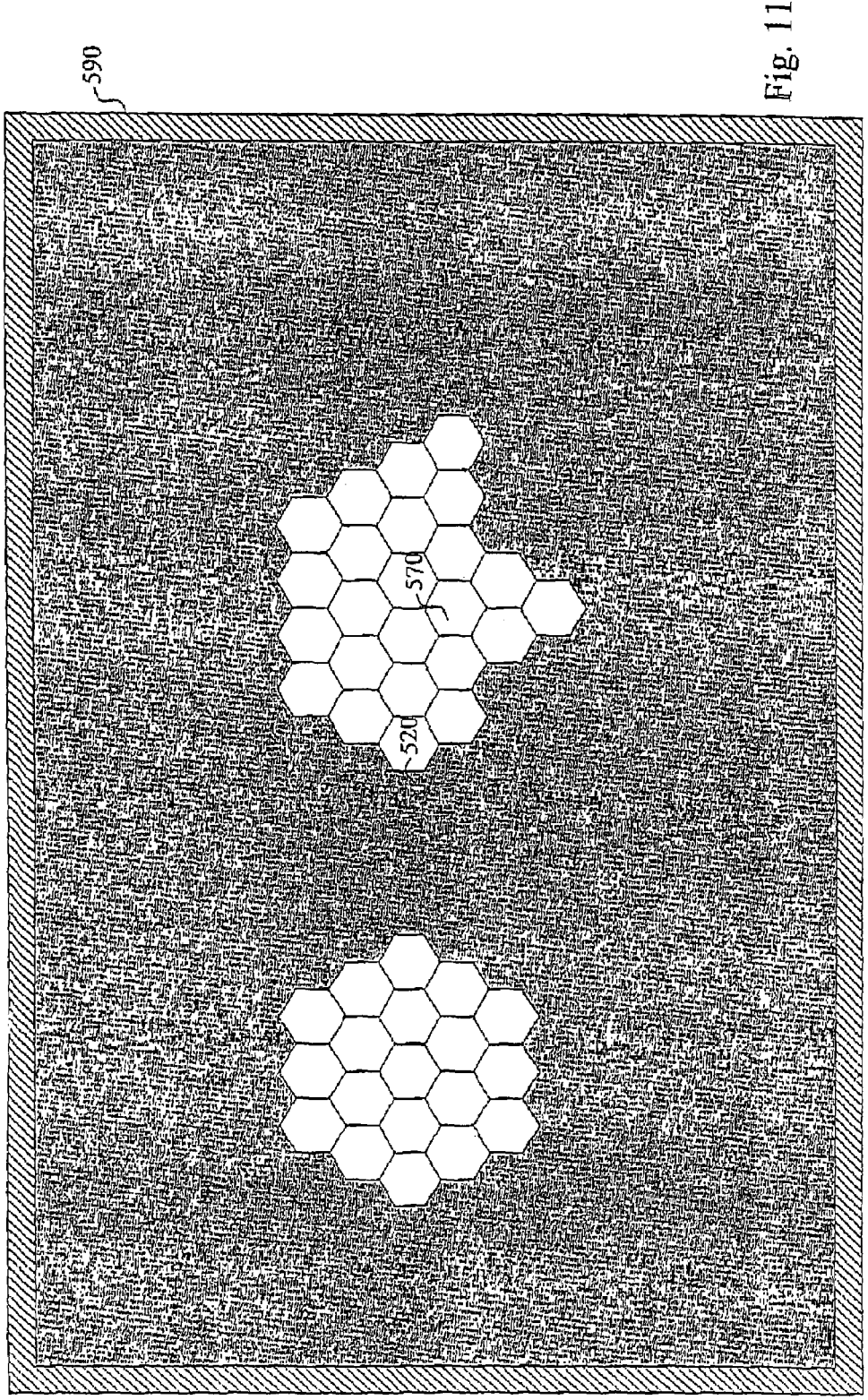
Figure 12:
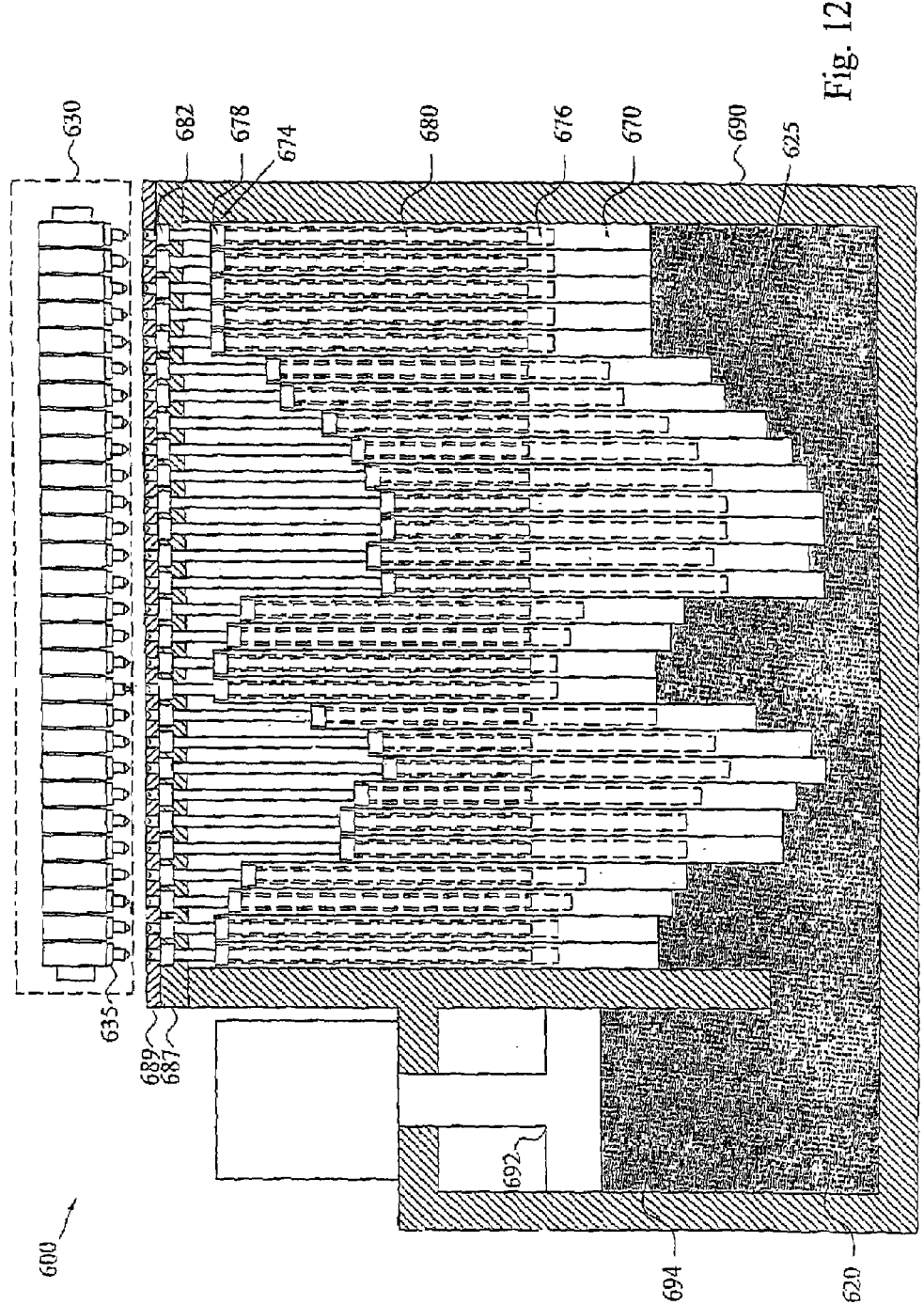
Figure 14:
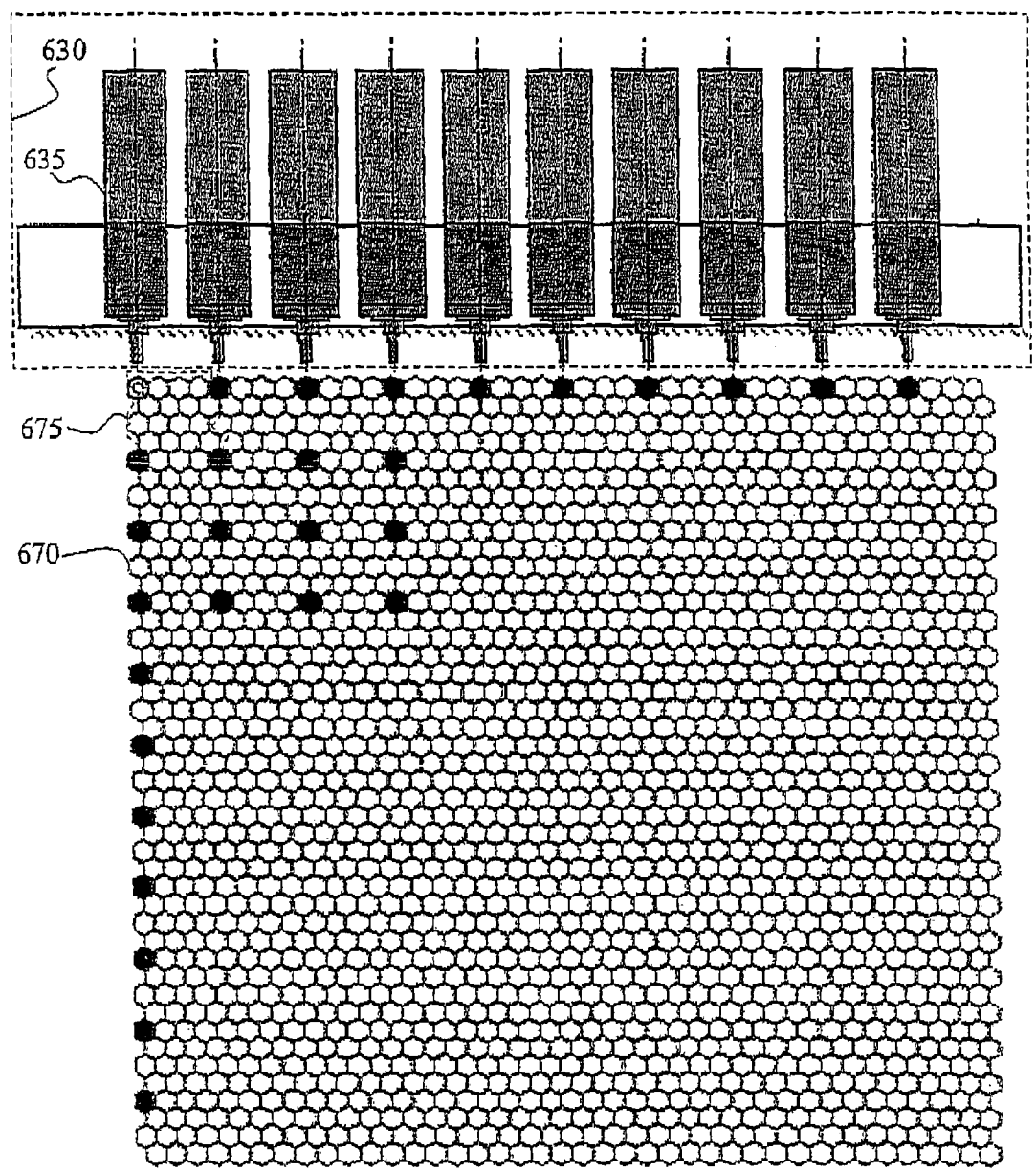
Figure 15:
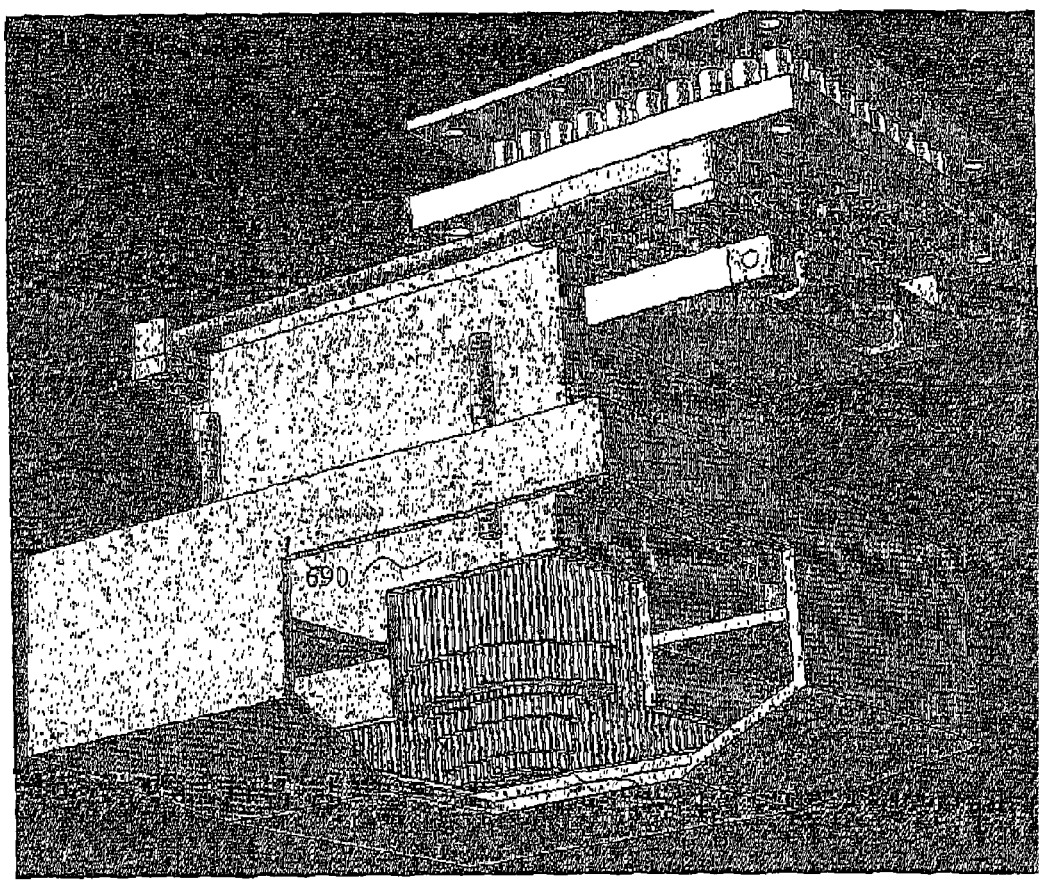
Figure 16:
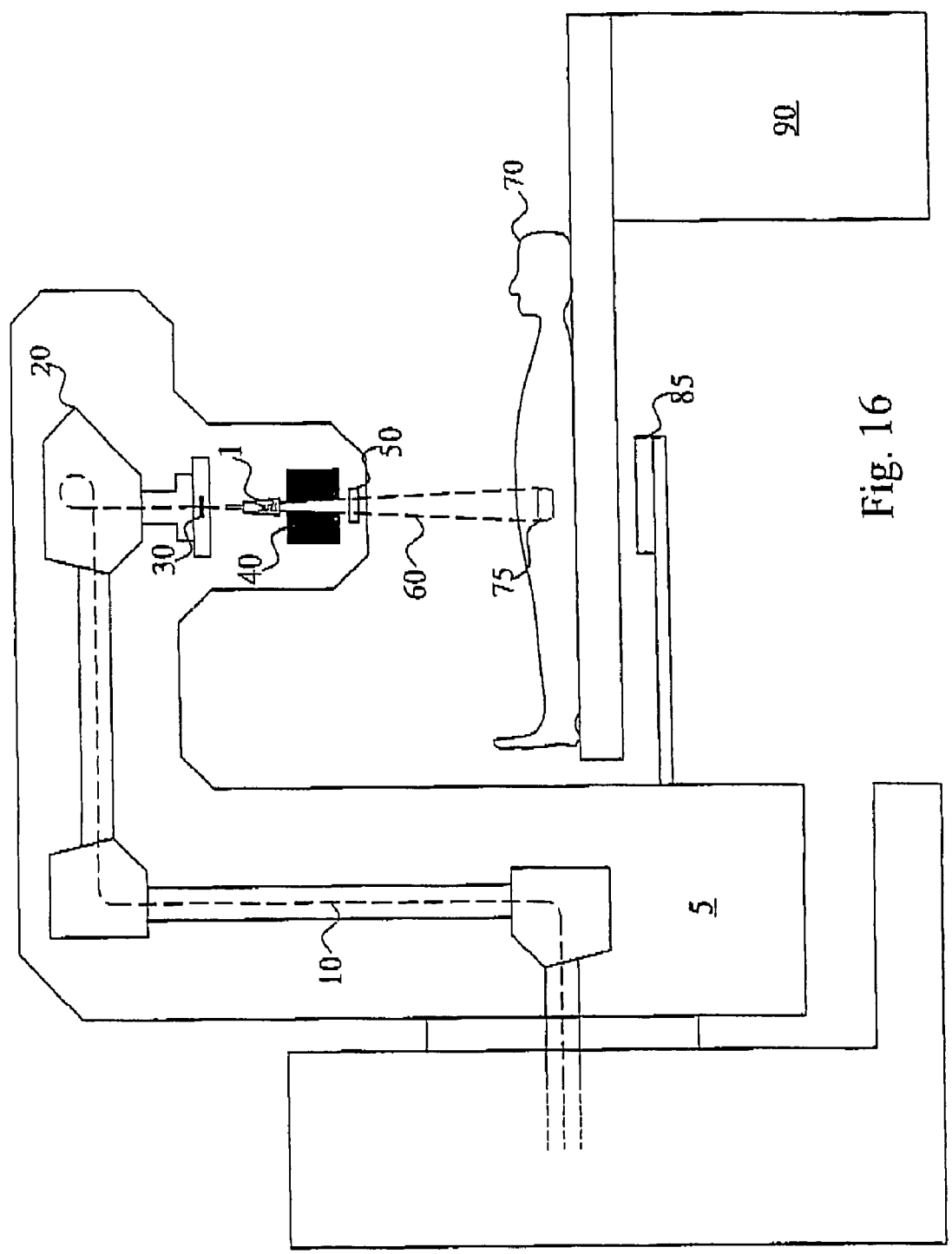
Figure 17:
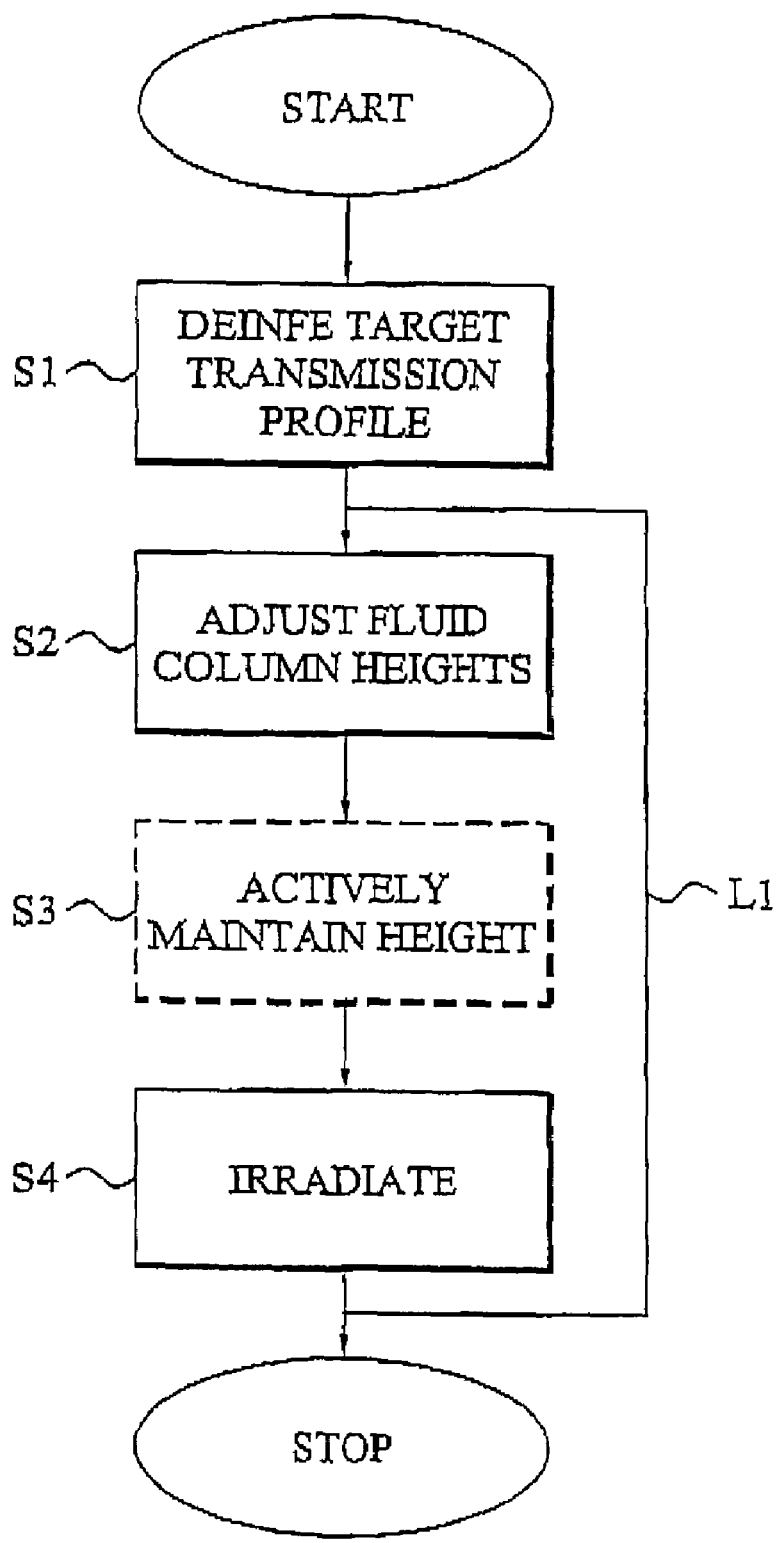
Figure 18:
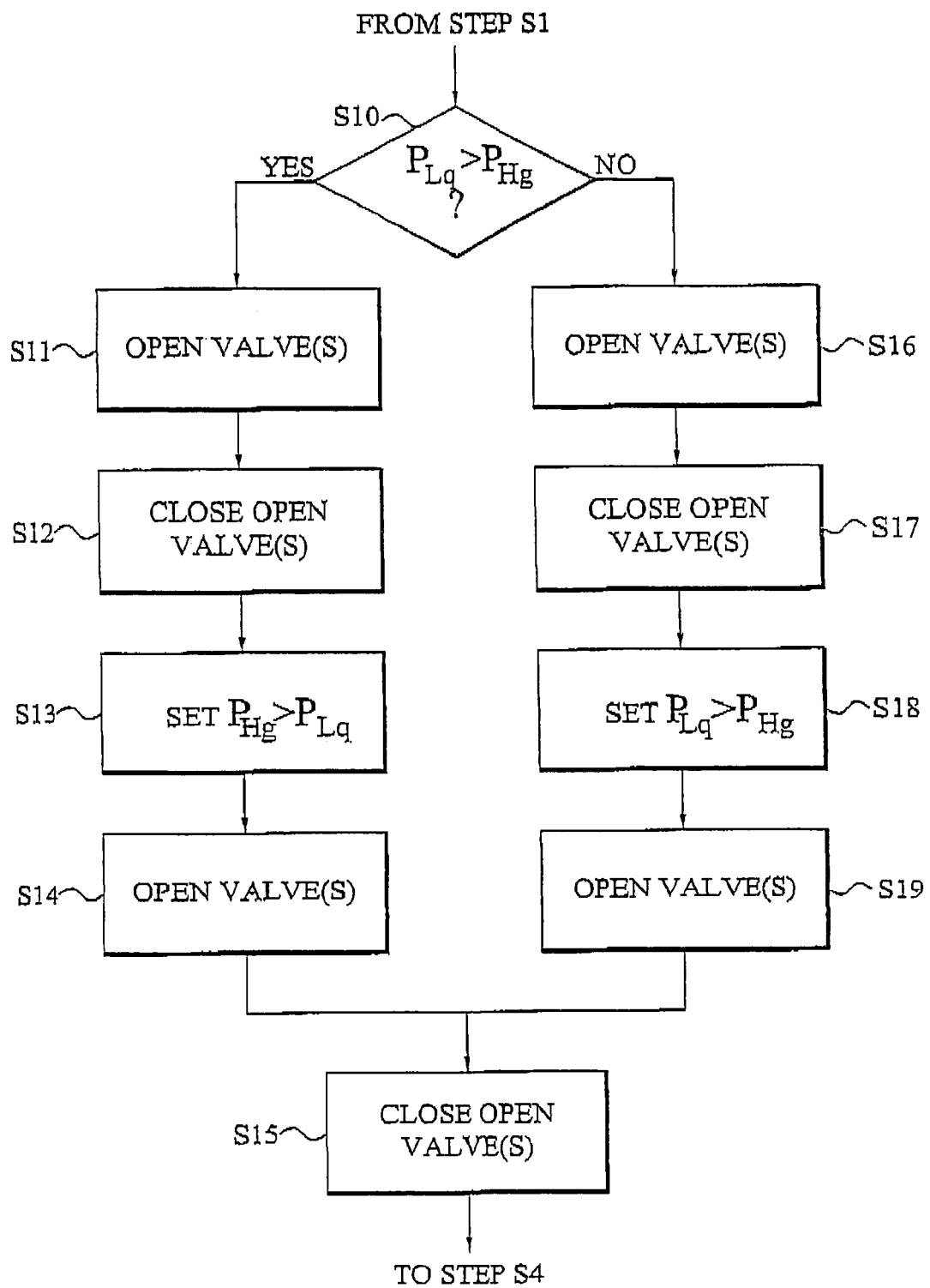
Figure 19:
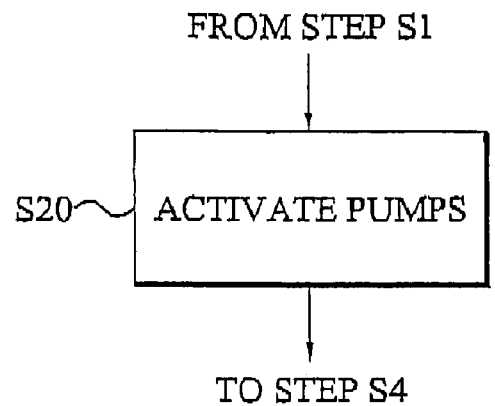
Figure 20:
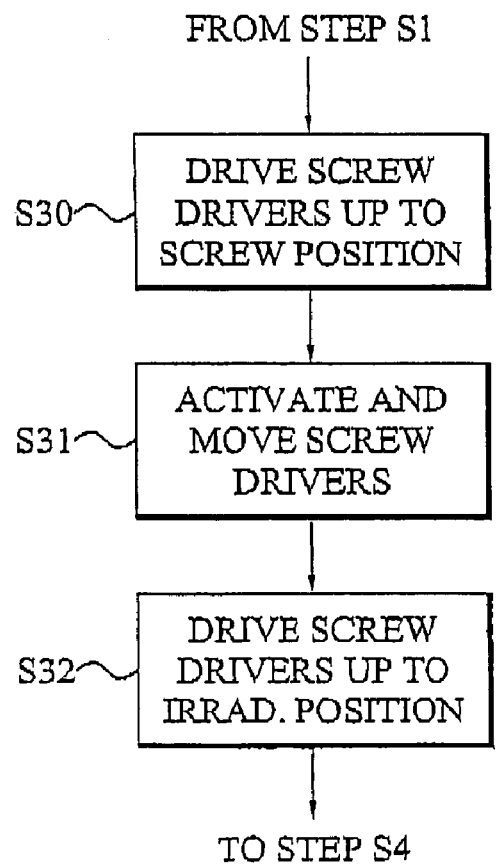

FIG. 3 schematically illustrates the irradiation geometry of the radiation beam modulator of FIG. 1;

FIG. 4A is a diagram comparing the convergence of the ratio of total number of segments (E(n)) and the total number of capillaries (N(n)) for hexagonal and square capillaries;

FIG. 4B is a diagram comparing lost modulation area as a function of capillary wall thickness for hexagonal and square capillaries;

FIG. 5A is a diagram illustrating the required capillary length to achieve an intensity ratio of 100% with a mercury/water and mercury/hexane system;

FIG. 5B is a diagram illustrating modulation windows for different capillary lengths as a function of energy;

FIG. 6 illustrates a second embodiment of a radiation beam modulator according to the present invention;

FIG. 7 illustrates a Gird embodiment of a radiation beam modulator according to the present invention;

FIG. 8 illustrates a fourth embodiment of a radiation beam modulator according to the present invention;

FIG. 9 illustrates a combined solution for the antagonizing fluid providing system;

FIG. 10 illustrates a fifth embodiment of a radiation beam modulator according to the present invention;

FIG. 11 is a cross-sectional view of the radiation beam modulator of FIG. 10 along the line B-B;

FIG. 12 illustrates a sixth embodiment of a radiation beam modulator according to the present invention;

FIGS. 13A-13E schematically illustrate the operation of the radiation beam modulator of FIG. 12 in more detail;

FIG. 14 schematically illustrates the organization of the bars of the radiation beam modulator of FIG. 12 and the operation of the screw driver system;

FIG. 15 is a three dimensional view of the radiation beam modulator of FIG. 12;

FIG. 16 is a radiation gantry equipped with a radiation beam modulator according to the present invention;

FIG. 17 is a flow diagram of the method of operating a radiation beam modulator according to the present invention;

FIG. 18 is a flow diagram illustrating an embodiment of the adjusting and maintaining steps of FIG. 17 in more detail;

FIG. 19 is a flow diagram illustrating another embodiment of the adjusting and maintaining steps of FIG. 17 in more detail; and FIG. 20 is a flow diagram illustrating a further embodiment of the adjusting and maintaining steps of FIG. 17 in more detail.

DETAILED DESCRIPTION

Throughout the drawings, the same reference characters will be used for corresponding or similar elements.

The present invention relates to a radiation modulator for modulating a radiation beam. The design of the radiation modulator is based on the concept of physical modulators in which non-uniform beam profiles are created by modulating the pry beam by a radiation modulating material having a thickness distribution corresponding to the desired transmission profile. The present invention utilizes a fluid as modulating material. The modulator includes an array of multiple, i.e. at least two, columns of this modulating fluid. A height adjuster is then provided for adjusting the heights of the multiple fluid columns. The so-adjusted columns will collectively form a radiation beam modulating profile having the desired thickness distribution. A radiation beam passing through the modulating profile of the fluid columns will then become modulated, resulting in a modulated radiation beam having a transmission profile corresponding to the desired target profile.

In a preferred embodiment of the invention, the height adjuster is adapted for dynamically and individually adjusting the heights of the multiple fluid columns. In another embodiment, the heights of groups of fluid columns can be adjusted (in real time) even though an individual column height adjustment is not possible. The actual height adjusting implementation employed depends, among others, on the required beam modulation resolution, the total cross-sectional area of the fluid columns, etc.

The modulating fluid employed according to the present invention is a fluid or liquid (deformable) medium having such a low viscosity that the medium is flowing at operation temperature. Basically, the low viscosity implies that the fluid can be pressed into and out from capillaries defining the columns or the fluid height can be adjusted by immersing and retracting bars in the fluid to adjust the fluid heights. This typically means that the fluid is preferably in liquid form at the operation temperature. Note that the fluid does not necessarily have to be in liquid form at room temperature, if an elevated temperature is employed for the operation of the radiation modulator according to the present invention. The fluid or liquid properties of the modulating fluid implies that once a desired modulation profile has been obtained by adjustment of the fluid column heights, these column heights should be maintained by the adjusting equipment or some dedicated unit in order to prevent a change of the modulation profile due to external forces, e.g. gravity and/or rotational forces, acting on the fluid.

In the following, the present invention will be mainly described in more detail in connection with a particular preferred type of beam modulation, namely radiation intensity modulation. In this type of modulation, the radiation beam to be modulated is typically a neutral particle beam comprising e.g. photons, neutrons, pions ($\pi_0$), etc. In such a case, the modulating fluid is preferably a high density fluid having radiation attenuating or absorbing properties. By then adjusting the column heights of the radiation attenuating fluid, the columns collectively form a desired radiation intensity modulating profile that can be used for modulating the intensity of the input radiation beam.

The radiation attenuating fluid employed for a radiation intensity modulator of the invention is preferably mercury that will be in liquid form at room temperature and a possibly elevated operation temperature. Mercury has two physical properties making it suitable for a dynamic physical modulator: high photon attenuation (Z=80, $\rho$=13.6 g/cm$^3$) and liquid phase at room temperature. However, the present invention is not limited thereto but could alternatively employ e.g. fluids based on tungsten powder or a fluid consisting of smooth and small spheres of a high photon attenuating material/metal. Furthermore, if elevated operation temperatures are employed, a fluid consisting of a metal or alloy having low melting point and high radiation attenuation can be employed. Typically examples include the fusible alloys denoted Rose's metal (50% Bi, 25-28% Pb and 22-25% Sn, melting point 100° C.) and Wood's metal (50% Bi, 25% Pb, 12.5% Sn and 12.5% Cd, melting point 70° C.).

Though, the present invention is well-adapted for radiation beam intensity modulation, it is not limited thereto. The modulator of the present invention could alternatively be a range or energy modulator adapted for modulating the range/energy of a radiation beam of charged particles, e.g. for ion therapy purposes. In ion beam therapy, the range of ions in tissue is determined by adjusting the energy of the incident ions. This is currently most often done in the prior art by interfering the beam with multiple Plexiglas discs of different thicknesses. A more flexible way would be to use a fluid-based modulator according to the present invention, in which the heights of the modulating fluid columns will collectively form a range modulating profile, in which the thickness distribution of the modulating fluid will determine the range/energy profile of the output and modulated charged radiation beam. In such a case, the radiation beam could include electrons, protons, ions, positrons, $\pi_+$, $\pi_-$ or other charged particles. The example of possible radiation attenuating fluids given above can also be used for range modulation.

A further, non-limiting example of a modulation type employable according to the present invention, is modulation of low energy photon beams, e.g. light modulation. In such a modulator, the modulating fluid consists of a high density fluid that has light attenuating or absorbing properties. By then adjusting the heights of the fluid columns different degrees of light attenuation can be obtained in different portions of the light beam.

Thus, the principles of the present invention, by employing an array of multiple columns of a radiation modulating fluid and then adjusting the heights of the fluid columns so that the columns collectively form a desired radiation beam modulation profile (thickness distribution profile), can be employed to different types of radiation beam modulations simply by selecting a modulating fluid that has modulating or attenuating properties adapted for the used radiation beam.

FIG. 1 is an illustration of a first embodiment of a radiation beam modulator 100 according to the present invention. This modulator 100 includes a core of multiple divergent capillaries 150 arranged in a bundle and a height adjuster 130 in the form of a liquid transport system for controlling the height of a radiation attenuating fluid 120 in the individual capillaries 150. In the figure only a single capillary 150 has been given a reference number in order to simplify the drawing. The multiple columns 125 of the radiation attenuating fluid 120 are, thus, defined by the inner channels of the capillaries 150. A respective first bottom end 152 of the capillaries 150 is in fluid connection with a reservoir 122 containing the radiation attenuating fluid 120 via a fluid channel or passage 124. This reservoir 122 is preferably a pressurizable reservoir 122 implying that a force can drive the fluid 120 from reservoir 122 through the channel 124 into the first ends 152 of the capillaries 150. This driving force could be provided by a simple piston 132 and (stepper) motor 134 for controlling the pressure exerted by the piston 132 on the fluid 120. This piston 132 and piston motor 134 constitutes a part of the height adjuster 130 employed for (individually) adjusting the height of the fluid 120 in the different capillaries 150 to form the target modulating profile.

The fluid reservoir 122 and fluid pressurizer 132, 134 are preferably arranged outside of the modulator core formed by the capillary bundle 150. This means that the fluid reservoir 122 and fluid pressurizer 132, 134 are preferably arranged outside of the input radiation beam 60 and outside of the resulting intensity modulated output radiation beam.

It is anticipated by the present invention that the modulator 100 can be equipped with more than one pressurized fluid reservoir or container 122. In such a case, the multiple reservoirs 122 can be arranged on a circumference around the capillary core and where each reservoir 122 is in fluid connection with the capillaries 150 through the fluid channel 124. Alternatively, different reservoirs 122 can be connected to different capillaries 150, implying that groups of capillaries 150 have there own dedicated fluid reservoir 122.

The height of the fluid columns 125 can be adjusted by further arranging a micro valve system (not illustrated) at the first ends of columns 152 and in connection with the fluid channel 124. By then opening an individual micro valve and driving the piston 132 into the reservoir 122, the radiation attenuating fluid 120 will be pressed into the capillary 150 associated with the open micro valve. This will, thus, increase the height of the particular fluid column 125. If the fluid column 125 should be decreased the micro valve of the column 150 is once again opened but now the piston 132 is retracted from the fluid 120 in the reservoir, i.e. no pressure is exerted. This will cause the fluid to flow from the capillary 150 back into the reservoir 122. The minimum height of a fluid column 125 that can be obtained with such an arrangement is dictated by the relative height position of the reservoir 122 and the capillaries 150 and possibly on the filling level in the reservoir 122.

As was noted in the foregoing, the fluid height in each capillary 130 is preferably individually adjustable in order to provide a high modulation resolution. However, for certain applications it might be enough to collectively adjust the heights of a subset of the multiple fluid columns 125. In such a case, the height adjustment is performed collectively for multiple columns 125 instead of for individual columns 125. In either case, the resulting fluid columns 125 collectively form a radiation beam modulating profile having a thickness distribution adapted to the desired intensity profile of the modulated radiation beam 60.

It is anticipated by the present invention that the modulating profile could be a two-dimensional profile. In such a case, the modulator core basically consists of (divergent) capillaries 150 arranged along a line. The radiation beam 60 to be modulated then preferably has a sectorial shape, which can be obtained by employing a colimator or other beam-restricting unit upstream of the modulator 100. However, in a preferred embodiment of the present invention, the modulating profile is a three-dimensional profile allowing usage of a conical radiation beam 60. In such a case, the intensity of the radiation beam 60 can be modulated to confine the delivered radiation dose to the tumor or target volume, while minimizing the dose of radiation to surrounding healthy tissue of adjacent healthy organs.

The height adjusting solution described above with a single fluid reservoir 122 and reservoir pressurizer 132, 134 works well for a horizontally arranged modulator 100. However, when arranged in a rotatable radiation gantry, the modulator 100 might be rotated, together with the gantry, to a non-horizontal position. In such a case, the fluid 120 may move slightly in the capillaries 150 resulting in a change of the radiation beam modulating profile. The so-changed modulating profile formed by the fluid columns 125 will have another thickness distribution than the intended target distribution, thereby resulting in an incorrect intensity modulation. The problem is solved by employing an antagonizing fluid, liquid and/or gas 140 and a separate supply system 135, 136, 138 for this antagonizing fluid 140. This antagonizing fluid 140 is a flowing fluid (has liquid or liquid/gas form at operation temperature) that has low radiation attenuation. If the antagonizing fluid 140 is to "float" on the radiation attenuating fluid 120 in the capillaries 150, the density of the antagonizing fluid 140 is preferably lower than that of the radiation attenuating fluid 120. This antagonizing fluid density 140 can, though, vary without significantly diminishing the intensity modulation window. Therefore, selection of antagonizing fluid will predominantly be based upon two properties; chemical compatibility with the interfacing materials (the radiation attenuating fluid 120 and capillary walls) and liquid flow properties. For intensity modulation purposes, the antagonizing fluid preferably also has as low radiation attenuation as possible. Suitable candidate fluids include, but are not limited to, hexane (non-polar), water or ethanol (polar) and purified kerosene. All these have low density and low viscosity.

As can be seen in FIG. 1, the radiation attenuating fluid 120 is entering the capillaries 150 from the first or bottom ends 152 thereof. The antagonizing fluid 140 then preferably enters the capillaries 150 from the opposite second or top ends 154 thereof. This means that each fluid column 125 will have a corresponding antagonizing fluid column 145 placed on top of the radiation attenuating fluid 120. The second ends 154 of the capillaries are in fluid contact, through one of more fluid passages or channels 144, with one or more antagonizing fluid reservoirs 142. This at least one antagonizing fluid reservoir 142 is preferably a pressurized reservoir 142, i.e. has equipment 136, 138 for forcing the antagonist fluid 140 from the reservoir 142 into the capillaries 150. This pressurizing equipment 136, 138 can simply be implemented by a piston 136 and piston driving motor 138, similar to the radiation attenuating fluid reservoir 122.

The two pressurizers 132, 134 and 136, 138 form the height adjuster 130 of the modulator 100 together with a micro valve system 135 arranged in connection with the second ends 154 of the capillaries 150. This micro valve system 135 could alternatively or in addition be arranged in connection with the first ends 152 of the capillaries. Different micro valve solutions are possible according to the present invention. However, the micro valve system 135 should be made of radiation resistant material to increase the life time of the modulator 100. A suitable micro valve system 135 that can be used according to the present invention is described by Watanabe and Kuwano in a document [3], the teaching of which is hereby incorporated by reference. That micro valve system 135 utilizes a high density micro valve matrix based on piezoelectric technology for precise control of a fluid flow. Other solutions that allows an individual control of the flow of antagonizing fluid 140 from the fluid reservoir 142 (or the flow of radiation attenuating fluid 120 from the fluid reservoir 122) to a particular capillary 150 or group of capillaries 150 can alternatively be used according to the present invention.

The height of an individual fluid column 125 is then determined by the opening time of the micro valve 135 associated with the relevant capillary 150 and the respective exerting pressure of the two fluid pressurizers 132, 134 and 136, 138. For example, in order to increase the heights of some radiation attenuating fluid columns 125, the pressure exerted by the pressurizer 132, 134 of the radiation attenuating fluid reservoir 122 is set higher than the corresponding pressure exerted by the pressurizer 136, 138 of the antagonizing fluid reservoir 142. When the micro valves 135 associated with the relevant columns 125 are open, the radiation attenuating fluid 120 will be forced from its fluid reservoir 122 via the channel 124 into the first ends 152 of the capillaries 150 having opened associated valves. The entering radiation attenuating fluid 120 will force (some on the antagonizing fluid 140 out from the capillaries 150 and into the antagonizing fluid reservoir 142. The respective height of these adjusted fluid columns 125 depends on the open time of the associated micro valves 135. Once a correct height has been obtained for a column 125, the associated micro valve 135 is closed. Correspondingly, when lowering the heights of some fluid columns 125, the pressure of the antagonizing fluid pressurizer 136, 138 is set higher than the pressurizer 132, 134 of the radiation attenuating fluid 120. When a micro valve 135 then is opened, the antagonizing fluid 140 will be pressed from the reservoir 142 through the fluid channel 144 and the open micro valve 135 into the upper end 154 of the capillary 150. The antagonizing fluid 150 pushes some of the radiation attenuating fluid 120 out from the capillary 150 (i.e. basically replacing the topmost portion of the radiation attenuating fluid 120 in the capillary 150) into the fluid reservoir 122. In this case, the open time of the micro valve 135 will determine how much the column height is decreased.

The height adjuster 130 together with antagonizing fluid 140 has, in addition to its participation in regulating the height of the radiation attenuating fluid columns 125, a further function in that they fix, once the micro valves 135 are closed, the radiation attenuating fluid 120 in the capillaries 150. This means that once a desired thickness distribution has been obtained, the antagonizing fluid 140 and the height adjuster 130 actively maintains the adjusted column heights. As a consequence of this fixing or locking property, the modulator 100 can be moved in a non-horizontal position without any movement of the radiation attenuating fluid 120 within the capillaries 150 and, thus, without any undesired change in the modulating profile. This is a major advantage compared to the prior art re-shapable modulator disclosed by Xu et al. [1]. Their modulator lacks any such equipment for actively maintaining the adjusted column heights, making their modulator unsuitable for any non-horizontal application.

In FIG. 1, the radiation attenuating fluid 120 occupies the lower part of the capillaries 150 with the antagonizing fluid 140 occupying the remainder upper part. However, the present invention is not limited thereto. In another embodiment, the contents of the two fluid reservoirs 122, 142 can be inter-changed so that the radiation attenuating fluid 120 is entering the capillaries 150 from the top ends 154 and the antagonizing fluid 140 enters from the bottom ends 152. The actual implementation to use depends on the properties (among others the densities) of the two fluids 120, 140 and does not affect the operation of the modulator 100.

FIG. 2 is a cross-sectional view of the capillary core 160 of the modulator 100 of FIG. 1 along the line A-A. As can be seen in FIG. 2, the capillaries 150 in the bundle 160 are preferably packed tight together so that no free space is available between the outer capillary walls. The reason for this is to me the amount of radiation that will pass unmodified through the capillary core 160. Different cross-section profiles of the capillaries 150 are possible in order to provide this tight packing, including triangular, rectangular, quadratic and hexagonal cross-section. Also combinations of capillaries 150 having different cross-section profiles could be possible according to the present invention. However, in order to minimize the modulation area loss due to the capillary walls, a hexagonal cross-section is preferred as illustrated in FIG. 2 and discussed further below.

Also the cross-section of the inner channels 155 of the capillaries 150 could be hexagonal. However, when employing e.g. mercury as radiation attenuating fluid, the non-wetting behavior of mercury may lead to formation of rounded menisci at corners of the inner channel walls. This could cause leakage of the antagonizing fluid 140 down the edges and seriously disturb the stability of the system. In order to avoid this, the cross-section of the inner capital channel 155 is then preferably modified to have curved edges. In a first embodiment, the inner channel 155 has circular cross-section. In a second embodiment that minimizes the capillary wall area and, thus, the non-modulating area, the inner channel 155 has a quasi-hexagonal cross-section, i.e. basically a hexagonal cross-section but with curved edges. Other solutions with curved edges are also possible and within the scope of the invention.

Figure 2:
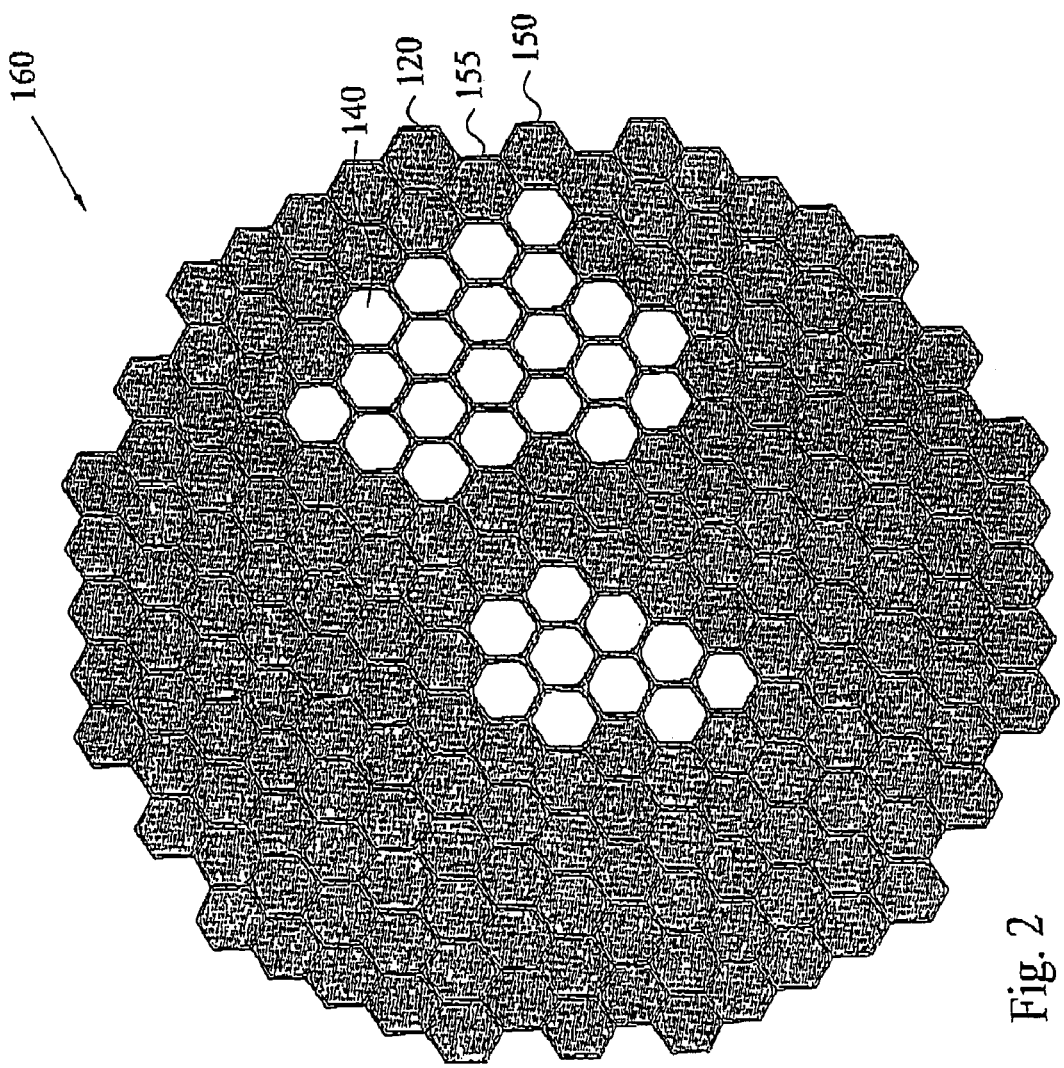
FIG. 2 is a cross-sectional view of the radiation beam modulator of FIG. 1 along the line A-A.

As is illustrated in FIG. 2, at a certain height of the capillary 150, some of the capillaries 150 may be filled with radiation attenuating fluid 120, whereas the remaining capillaries are then filled with antagonizing fluid 140. This means that the radiation beam passing through the capillary core 160 of FIG. 2 will have two high-intensity areas defined by the two islands of low heights of radiation attenuating fluid columns. The remaining portion of the beam, passing through larger radiation attenuating thicknesses, will then have a comparatively lower intensity.

The total size and shape of the capillary core 160 is preferably selected and adapted to the particular radiation beam to be modulated. However, the modulator of the invention can be used together with different radiation beam shapes by simply using a smaller or larger portion of the capillary core 160 for modulation purposes.

Modulator and Capillary Dimensions

With reference to FIG. 3, assume that the modulator core consists of N divergent capillaries and is placed at a distance SMD (source to modulator distance) from the beam source 30. The radius r(z) at a distance z down from the source is given by:

$$r(z) = z \tan \varphi = z \frac{r(SSD)}{SSD}, \quad (1)$$

where SSD is the source to skin distance. Furthermore, the cross-sectional area A and the total volume V of the modulator is given by:

$$A(z) = \pi r(z)^2 \quad z \in [SMD, SMD + H] \quad (2)$$

$$V = \pi \frac{r(SSD)}{12 \times SSD}((SMD + H)^3 - SMD^3) \quad (3)$$

In order to meet the demand of minimum spatial resolution, the beam field area BA=A(SSD) and the desired pixel (beam pixel) area α give the number of capillaries:

$$N = \frac{BA}{\alpha} \quad (4)$$

The vertically dependent cross-sectional area of individual capillaries will then approximately be:

$$\alpha(z) = \frac{A(z)}{N} \quad z \in [SMD, SMD + H] \quad (5)$$

Varying the parameters described gives different dimensions for the capillaries and values for a few reasonable settings are shown in Table 1.

TABLE 1

| BA cm² | τ_c cm | α cm² | N | SSD cm | SMD cm | φ rad | α_t mm² | α_b mm² |
|---|---|---|---|---|---|---|---|---|
| 25 × 25 | 14.1 | 0.25 | 2500 | 75 | 15 | 0.165 | 1.00 | 2.78 |
| " | " | 0.25 | 2500 | 100 | " | 0.124 | 0.5625 | 1.5625 |
| " | " | 0.35 | 1786 | 75 | " | 0.165 | 1.40 | 3.89 |
| " | " | 0.35 | 1786 | 100 | " | 0.124 | 0.787 | 2.187 |

BA = beam field size,
$\tau_c$ = corresponding radius of circular field,
α = bixel size,
N = number of capillaries,
SSD = source to skin distance,
SMD, source to modulator distance,
φ = maximum half angle,
$\alpha_t$ = capillary cross-sectional area at the top of the modulator,
$\alpha_b$ = capillary cross-sectional area at the bottom of the modulator.

Cross-Sectional Shape of Capillaries

When irradiating tumors, it is of vital importance that the whole target region is covered since all clonogenic tumor cells must eliminated. However, since tumor boundaries are irregular and the pixels being finite in size, healthy tissue will also receive dosage. In order to investigate the influence of cross-sectional geometry, the figure of merit fractional excessive area irradiated, ƒ=BA/TA, where BA and TA stand for beam area and target area, respectively, was calculated for two target geometries: circles and typical 2D prostate shapes. The bixel size was set to 25 mm² and equal for both geometries. Two shapes for capillary cross-section were considered: regular hexagon and square. The (arithmetic) mean gain factor $\bar{f}$ was defined by:

$$\bar{f} = \frac{1}{n}\sum_{i=1}^{n} \frac{f_{square}}{f_{hexagonal}} \quad (6)$$

$\bar{f}$ was calculated to 1.08 and 1.02 for circular and prostate shape, respectively, with n=9 for circular shape and n=4 for prostate shape. Thus, a hexagonal structure gives a slightly better 2D conformality compared to a square structure.

Since the capillary walls have finite size there will be an unmodulated part of the transmitted radiation beam. This lost modulation area will depend on capillary wall thickness t and on the efficiency of the tiling. It is mathematically proven that any partition of the plane into regions of equal area has a perimeter at least that of the regular hexagonal honeycomb tiling. However, to give a quantized perspective, an analytical comparison of hexagonal and square tiling efficiency is given below. In order to ease calculations the tiling is made by starting from a single tile/capillary, i.e. a hexagon or a square, and then in n steps adding tiles around the preceding ones, ending up with N(n) tiles (or capillaries) and a total of E(n) segments, each having length e (e depends on the type of tiling) and thickness t.

Hexagonal Tiling $$N(n) = 3n^2 + 3n + 1 \quad (7)$$

$$E(n) = 9n^2 + 15n + 6$$

$$\alpha = \frac{3\sqrt{3}}{2} e_{hex}^2$$

$$Q_{hex} = \frac{\alpha_{well}}{\alpha}$$

$$= \frac{t \times e_{hex} \times E(n)}{\alpha \times N(n)}$$

$$= \frac{2}{3\sqrt{3}} \frac{t}{e_{hex}} \frac{9n^2 + 15n + 6}{3n^2 + 3n + 1} \xrightarrow{n \to \infty} \frac{2}{\sqrt{3}} \frac{t}{e_{hex}}$$

Square Tiling $$N(n) = 4n^2 + 4n + 1 \quad (8)$$

$$E(n) = 8n^2 + 12n + 4$$

$$\alpha = e_{hex}^2$$

$$Q_{hex} = \frac{\alpha_{wall}}{\alpha}$$

$$= \frac{t \times e_{sq} \times E(n)}{\alpha \times N(n)}$$

$$= \frac{t}{e_{hex}} \frac{8n^2 + 12n + 4}{4n^2 + 4n + 1} \xrightarrow{n \to \infty} 2 \frac{t}{e_{sq}}$$

Since the expression $E(n)/N(n)$ converges at a fast rate for both geometries, see FIG. 4A where the curve 80 represents hexagonal-filing and the curve 82 represents square tiling, the limit values are used in the calculations. Combing equations (7) and (8) and using the relation $e_{sq}=3^{1/4} \times 2^{-1/2} \times e_{hex}$ for the same bixel area yield the relative efficiency of the respective tilings:

$$\frac{Q_{sq}}{Q_{hex}} = \frac{e_{hex}\sqrt{3}}{e_{sq}} = \frac{2^{1/2}}{3^{1/4}} \approx 1.075 \quad (9)$$

Thus, square tiling gives 7.5% more loss of modulation area than hexagonal tiling. The absolute percentage area lost in the different tilings as a function of wall thickness was calculated for the prototype values defined in Table 1 and the result is displayed in FIG. 4B, in which the line 84 represent square tiling and the line 86 represent hexagonal tiling.

Furthermore, for the same surface density of elementary beams, a hexagonal tiling results in less fluence variations on small-scale beam heterogeneity than a square tiling. In summary these results, suggests that a hexagonal capillary cross-section is preferred over a square cross-section since less overdosage will be delivered to healthy tissue, it minimizes the capillary wall material, hence maximizes the cross-sectional modulation area, and the small-scale beam homogeneity is better.

Capillary Length

In order to achieve high dose gradients and to meet the desired demand for beam modulation of 100-1%, the capillaries should have some minimum length $h_{min}$. This length is given by the difference in attenuation between radiation attenuating fluid and the antagonizing fluid and is therefore energy dependent, A measure of $h_{min}$ is obtained by considering transmission of primary photons traveled through equal thickness of radiation attenuating fluid and antagonizing fluid (without any flattening filter):

$$h_{min} = \frac{\ln R + \ln \Phi(\theta_{max})^{-1}}{\mu_{att}\rho_{att} - \mu_{anta}\rho_{anta}} \quad (10)$$

where $$R = \frac{I_{max}}{i_{max}},$$

I is the intensity, $\Phi(\theta_{max})$ is the normalized fluence output from the source at the edge of the field and is given by $$\Phi(E, \theta) = \frac{\Phi(E, 0)}{1 + \left(E\frac{\theta}{a}\right)^b},$$

E is the maximum photon energy in MeV, the constants $\alpha=1.73$ rad×MeV and b=1.4, $\mu$ is the mass attenuation coefficient and $\rho$ is the density.

Calculations of the total capillary length were performed for the systems mercury/water and mercury/hane. The results show that the maim length needed for a modulation of 100-1% occurs for the beam energy 4.1 MeV and amounts to approximately 9 cm, see FIGS. 5A and 5B. FIG. 5A illustrates the required capillary length to achieve an intensity ratio of 100% with the systems mercury/water (curve 81) and mercury/hexane (curve 83). FIG. 5B illustrates the modulation windows for different capillary lengths as a function of energy.

As was noted in the foregoing, the capillaries are preferably divergent as is evident from FIG. 1 in order to give a spatially invariant penumbra. This in turn enables steeper dose gradients.

Capillary Material

It is a general goal to keep the walls of the capillaries thin in order to minimize the non-modulating area. Various materials and fabrication processes can be considered, but the seemingly most reasonable are sintering, etching and wire-sparkling metals. Also, metals are in general highly resistant to radiation-induced damage.

Secondly, the material must be resistant to any metallurgical attack that could be caused by the radiation attenuating fluid, especially when employing mercury (corrosion and formation of alloys). Last but not least, since the capillary walls are passive they will appear in the transmission profile as a positive or negative hexagonal grid. This phenomenon is similar to the problem with interleaf leakage in multileaf collimator systems. However, the transmission through capillary walls will be dependent on the is material selected. A too high transmission (too low attenuation coefficient of the capillary material) would increase the risk of exceeding tolerance levels for healthy tissues, while a too low transmission (too high attenuation coefficient) would increase the risk of local tumor cell survival. Although scattering and the finite source size will help to smooth the profile, the effect cannot be neglected.

The effect of three different wall materials, 316L stainless steel, aluminum and titanium, on small-scale transmission profiles was analyzed. Stainless steel gives good homogeneity at low transmissions, but too large dips when high transmissions are desired. With aluminum the effect is negated. From this aspect, titanium had the best properties and can therefore be a suitable capillary wall material.

Determination of the Height/Thickness of the Radiation Attenuating Fluid

In a first approximation scattering is neglected and the discrete fluid thickness distribution T is a function of the desired fluence profile $\Phi_d$ and the primary photon fluence incident on the modulator $\Phi_0$. The relation is given by:

$$T = \frac{\ln(\Phi_0/\Phi_d) - \mu_{anta}H}{\mu_{att} - \mu_{anta}} \quad (11)$$

For a more accurate calculation, scattered photon fluence should be taken into account. The radiation attenuating fluid thickness would then be determined by the relation:

$$\Phi_d(r,T) = \Phi_p(r,T) + \Phi_s(r,T) \quad (12)$$

where $\Phi_d(r,T)$ is the desired fluence profile, $\Phi_p(r,T)$ is the primary attenuated transmission and $\Phi_s(r,T)$ is the scattered contribution.

The thickness of the radiation attenuating fluid can be verified by different methods, including both direct measurements and indirect measurements (by monitoring the transmission profiles).

Depending on the method of flow control, different approaches to fluid column height measurements will be beneficial. A first approach is cavity resonance, in which radio frequency waves are sent down the capillaries. A correlation between the measured resonance and the fluid thickness can be determined. Overhearing between capillaries can be minimized by using different frequencies for neighboring capillaries. In another approach, reflection techniques are employed. This approach is suitable in cases where the radiation attenuating fluid has significantly different acoustic impedance compared to the antagonizing fluid. The thickness would then be determined by the time. Also optical methods are possible, employing laser or LED (light emitting diode) techniques. Furthermore, time-distance based measurements could be used.

An indirect method of measuring the fluid thickness distribution would be to place a detector with high resolution below the modulator, measure the spatial transmission and perform an inverse calculation. The difference $\Delta\Phi$ between the desired $\Phi_d$ and measured $\Phi_m$ intensity maps would then yield a correction factor $\Delta T$ for the thickness distribution:

$$\Delta\Phi = \Phi_d - \Phi_m \Rightarrow \Delta T = \Delta T(\Delta\Phi) \quad (13)$$

Also, the measured post-modulation profile could be compared to electronic portal imaging device (EPID) measurements to make real-time improvements of the fluid thickness distributions and to enhance the estimations of delivered dose distributions in the patient. The selection of detector type should be made by considering the trade-off of having low attenuation and scattering against providing good accuracy. Ion chambers may be the optimum choice since the attenuation is minimal and the count rate is high.

FIG. 6 schematically illustrates another embodiment of a radiation modulator 200 according to the present invention. This modulator 200 comprises a similar capillary core as the embodiment discussed above in connection with FIG. 1. The system of providing the radiation attenuating fluid 220 from one or more fluid reservoirs 222 include, as in FIG. 1, a pressurizer illustrated in the form of a piston 232 and piston 234 for exerting a force that, drives the radiation attenuating fluid 220 from the reservoir 222 via a fluid channel 224 to the first or bottom ends 252 of the capillaries 250.

Instead of employing a micro valve system as a part of the height adjuster 230 as in FIG. 1, this modulator embodiment utilizes a system of valves 235 with associated valve motors 233, of which two are illustrated in the figure. The valves 235 are preferably inter-connected with a fluid channel 237 and are further connected to at least one reservoir 242 for the antagonizing fluid 240, preferably a pressurized reservoir 242 having a fluid pressurizer 236, 238. In a preferred embodiment of the invention, each capillary 250 is in fluid contact, via its second or top end 254, with a respective valve 235 through a fluid channel 244. In another embodiment of the invention, a group of capillaries 250 are connected to a single valve 235.

The electromechanical devices, i.e. valves 235 and valve motors 233, are preferably mounted around and outside of the radiation field, e.g. by being provided along a circumference of a circle having a diameter larger than the diameter of the radiation beam. In applications with a rather large capillary core and many capillaries, the valves 235 and motors 233 could be distributed not only around the capillary core but also on different layers, i.e. on top of each other as is illustrated in the figure.

The operation of the modulator 200 for adjusting the heights of the fluid columns 225 and obtaining a target modulation profile and fluid thickness distribution is similar to the embodiment of FIG. 1. Thus, the respective column heights are defined by the open time of the valves 235 and the pressure difference between the pressurizer 232, 234 of the radiation attenuating fluid reservoir 222 and the pressurizer 236, 238 of the antagonizing fluid reservoir 242. Thus, if the pressure exerted by the pressurizer 232, 234 is larger than the pressure of the antagonizing pressurizer 236, 238, radiation attenuating fluid 220 will flow from the reservoir 222 via the channel 224 into a capillary 250 if the valve 235 associated with the capillary 250 is open. In addition, antagonizing fluid 240 in the capillary 250 will flow out through the channel 244 and via the valve system into the reservoir 242. As a result, the column height will be increased. The opposite procedure is performed when lowering the column height.

FIG. 7 illustrates a further embodiment of a radiation beam modulator 300 according to the present invention. The core of capillaries 350 and the reservoir 322 for the radiation attenuating fluid 320 and the fluid transport system 324 and pressurizer 332, 334 are similar to FIG. 1 and FIG. 6 and are not described in more detail.

In this embodiment, preferably each capillary 350, or at least each group of multiple capillaries 350, has its own pump 336, 338 and antagonizing fluid reservoir 342. In the figure, the pumps 336, 338 have schematically been illustrated as a piston 336 and a piston driving motor 338. The pump and reservoir system is preferably provided around and outside of the radiation field, possibly on different layers as in the figure. The piping can for instance be done by etching small channels 344 from the upper ends 354 of the capillaries 350 to the pumps 336, 338 and packing them in layers.

Different pump solutions can be employed according to the present invention, including micro pumps in the form of stepper motors 338 driving an associated piston 336. Such pumps can be made small with satisfactory accuracy and reliability. In addition, the position of the pistons gives a direct measurement of the surface position of the radiation attenuating fluid 320. Also piezo-actuators or -pumps can be employed. Another pump technique could be to use bubble pumps that traditionally are employed in inkjet technology. These inkjets can dispense ink blobs at frequencies in the order of kHz with nanolitre precision. The inkjet head dispenser includes a small 110 chamber with inlet and outlet holes. After the ink has entered the chamber, heating causes an overpressure to sling a well defined ink drop on the paper. A capillary 250 could then have two antagonizing bubble pumps based on inkjet technology, one in each direction. In order to minimize transient effects and to increase precision, the pumps could be constantly at work. The resulting flow would then be given by the difference in working frequency. When driven at the same frequency, equal amounts of fluid will leave the capillary 350 as will enter.

The height of a fluid column 325 in a capillary 350 may then be adjusted by the height adjuster 330 by pumping antagonizing fluid 340 into or out from the capillaries 350. In the former case, the antagonizing fluid 340 will push the radiation attenuating fluid 320 partly out from the capillaries 350 and into the reservoir 320. As a consequence, the column heights will be lowered. In the latter case, the antagonizing fluid 340 is drawn from the capillaries 350 into the reservoirs 342. Simultaneously, radiation attenuating fluid will be drawn from the reservoir 320 into the capillaries 350, resulting in a column height increase. Individual pumps 336, 338 can operate by pumping antagonizing fluid 340 into some capillaries 350 simultaneously as other pumps 336, 338 draws antagonizing fluid 340 from other capillaries 350.

The usage of a single fluid reservoir and pressurizer for the radiation attenuating fluid and multiple reservoirs and pumps for the antagonizing fluid can be interchanged, as is shown by the embodiment of the modulator 400 illustrated in FIG. 8. Each capillary 450, or group of capillaries 450, is in fluid contact, via its lower end 452, to a respective fluid channel 424 and fluid reservoir 422. A pump 432, 434, being a part of the height adjuster 430, is connected to the reservoir 422 in order to pump radiation attenuating fluid 420 into or out from the capillary 450. The mounting of these pumps 432, 434 and reservoirs 422 is similar to the embodiment of FIG. 7, but is preferably arranged outside and around the lower part of the modulator core instead of the upper part thereof. The upper ends 454 of the capillaries 450 are in fluid contact, via one or more fluid channels 444, to one or more antagonizing fluid reservoirs 442, which preferably are pressurized reservoirs 442.

The embodiments employing micro valves and pumps described in the foregoing can be combined as is schematically illustrated in FIG. 9. In the previous embodiments, the modulator would typically have to be taken out of action if one of the valves or pumps breaks down. This combined solution lowers the probability of breakdown by integrating the controlling devices in groups. This means that a reservoir 342 of antagonizing fluid 340 is in fluid contact with a group of capillaries 350, via the fluid channel 344. A stepper motor 338 associated with the reservoir 342 then supply pressurized antagonizing fluid 340 to this capillary group. Each such capillary group is associated with a micro valve system 355 for individual capillary control. This means that the antagonizing fluid 340 provided from the reservoir 340 by the pump 338 is individually portioned out in the capillaries 350 of the group by opening and closing the individual micro valves 355.

FIG. 9 further illustrates in more detail how the pumps 338, reservoirs 342 and fluid channels 344 can be arranged outside of and around the capillary core 360.

Other combinations of the modulator embodiments of FIGS. 1, 6-8 are also possible and within the scope of the present invention.

FIG. 10 illustrates an embodiment of the radiation beam modulator 500 according to the present invention that does not utilizes any antagonizing fluid but instead has a bath 590 containing the radiation attenuating fluid 520. Multiple low radiation attenuating bars 570 are immersed in this fluid bath 590. The height adjuster 530 then controls the level of immersion of the bars 570 in the fluid 520 and adjusts this bar immersion to obtain the desired modulation fluid profile and fluid distribution thickness of the modulator 500.

In this embodiment of the modulator 500, the height adjuster 530 includes wire motors 535 arranged outside of and possibly around the radiation beam and modulator core. Each such wire motor 535 is connected to and controlling one or more wire loops 580, where a first end 584 of the wire 580 is connected to the upper end 574 of a bar 570 and a second end 582 of the wire 580 is connected to the bottom end 572 of the bar 570. The bottom of the fluid bath or container 590 includes a matrix or array of holes, through which the wires 580 can pass. These holes are preferably made fluid-tight for preventing the radiation attenuating fluid 520 from leaking through the holes in the bath 590.

The fluid bath 590 contains or is in fluid contact with at least one fluid reservoir 594, in which the radiation attenuating fluid 520 can be pushed when the bars 570 are immersed further into the fluid, 520. The reservoir 594 can optionally be provided with a piston 592 and possibly a piston motor for exerting a fluid counter pressure.

After immersing the different bars 570 in order to obtain the target modulating profile and fluid thickness distribution, the bars 570 can optionally be squeezed tight together. This will both is the geometry of the bars 570 and the radiation attenuating fluid 520 and also prevent fluid 520 from leaking up between the bars 570. This bar squeezing or packing could be performed actively by a dedicated bar packing equipment (not illustrated). Alternatively, the bath walls and bar profiles could be mutually adapted to each other so that the bars 570 are kept packed close together without any actively operating squeezing equipment.

A column 525 of the radiation attenuating fluid 520 is defined as the part of the fluid bath that is positioned directly below a given bar 570, i.e. the portion of the fluid that occupies the volume from the bottom end 572 of the bar 570 to the bottom of the bath 590. On the contrary to the previous modulator embodiments, the fluid columns 525 of this embodiment are interconnected, i.e. not separated by any intermediate capillary walls. This means that a continuous modulating profile that does not include any non-modulating gaps will collectively be formed by the fluid columns 525.

The adjusted column heights are actively maintained between adjustment occasions by the bars 570, which in turn are kept in position by the wire loops 580 and the w motors 535.

As was noted above, the bars 570 are made of a low radiation attenuating material for the case with intensity modulation of a radiation beam. The bar material should further have high radiation hardness and resistance to cope with the input radiation to be modulated. In addition, the bars 570 should be resistant to any metallurgical attacks by the radiation attenuating fluid 520. Suitable bar material includes metals with low atomic number, such as beryllium. Furthermore, radiation-resistant plastics could be employed.

In order to simplify immersion of the bars 570 in the fluid 520 and pushing aside the fluid 520 during the immersion, the lower ends 572 of the bars 570 could be somewhat rounded.

Different cross-sectional profiles can be employed for the bars 570, similar to the cross-sections of the capillaries in the foregoing embodiments. Thus, the bars 570 could, for example, have rectangular or square cross-sections. However, in a preferred embodiment of the invention, hexagonal bars 570 are preferably employed in order to preserve the benefits from the hexagonal structure discussed above in connection with FIGS. 4A and 4B.

However, unlike the divergent capillaries of the previous embodiments, the non-divergent bars will yield a spatially dependent penumbra, which may set limits on the dose gradients. In addition, the projected resolution will vary with bar height. This can be solved by arranging a thin peripheral collimator, e.g. a 15 mm tungsten leaf collimator, downstream of the radiation modulator 500. This collimator can then be employed for defining the edge of the modulated radiation beam and results in sharper penumbra.

FIG. 11 is a cross-sectional view of a part of the radiation modulator 500 of FIG. 10 along the line B-B. In this figure, the honeycomb structure of the low radiation attenuating bars 570 is clearly visible. The particular modulation profile represented by FIG. 11 has two regions with low heights of the columns of the radiation attenuating fluid 520. This means that the portions of the radiation beam that passes through these two low attenuating islands will have higher intensity that the remaining parts of the beam that passes through larger fluid thicknesses.

FIG. 12 illustrates another embodiment of the radiation modulator 600 of the invention that utilizes low radiation attenuating bars 670 immersed in a bath 690 with the radiation attenuating fluid 620. In this embodiment, the fluid reservoir 694 and fluid pressurizer 692 are similar to the embodiment in FIG. 10.

The multiple bars 670 have a respective blind bore or blind hole 676 in their first or upper end 674. This means that the bore or channel 676 runs into a certain depth of but not through the bar 670. The bar 670 further has a nut 678 arranged in connection with the blind bore 676, preferably at or close to the upper end 674 of the bar 670.

At the top of the fluid bath 690 is one or more low radiation attenuating plates 687, 689 arranged similar to a lock on a container. Multiple screws 680 are attached to and fixed by the plates 687, 689 through their screw heads 682 so that the screws 680 cannot move vertically but still be rotated. Each such screw 680 runs in a respective blind bore 676 of a bar 670 through the nut 678 of the bar 670.

The tight packing or squeezing together of the bars 670, obtained either trough a dedicating actively operating equipment or due to the particular design of the bars 670 and the bath 690 and the organization of the bars in the bar bundle or core, will prevent the bars 670 from rotating. Thus, since a bar is locked between its neighboring bars (see the honeycomb structure of FIG. 11), the bar can move vertically (immerse into or retract from the fluid) but not rotate. This means that when the screw 680 associated with a particular bar 670 is rotated or screwed, this rotating motion will cause the bar 670 to move upwards towards the screw head 682 or downwards away from the screw head 682. As a consequence, the level of immersion of a bar 670 in the radiation attenuating fluid 620 and, thus, the height of the fluid column 625 directly below the bar 670, is adjusted by rotating the screw 680.

In this embodiment of the modulator 600, the height adjuster 630, thus, includes a screw driver and preferably a set of multiple screw drivers 635 as illustrated in the figure. The screw driver system could be arranged in a similar array or matrix as the bar core, implying that there is one screw driver 635 for each screw 680 and bar 670. However, in embodiments with rather larger modulator cores, the number of screw drivers 635 can be less than the number of screws 680 and bars 670. In such a case, the screw drivers 635 can (step-by-step) move between the screws and individually setting the desired bar immersion of a bar 670 by rotating the screw head 682 associated with the bar clockwise or counterclockwise (or not at all if the bar already has the correct immersion level).

Once the bar immersion has been adjusted, the bars 670 locks the radiation attenuating fluid 620 in position of the obtained modulation profile. In other words, since the bars 670 are fixed via the screws 680 to the upper plates 687, 689, they prevent the fluid 620 from unintentionally moving e.g. in the case of the modulator 600 is rotated.

The same bar material and bar cross-sections as was described in the foregoing in connection with FIG. 10 apply to the modulator embodiment of FIG. 12.

Figure 13A:
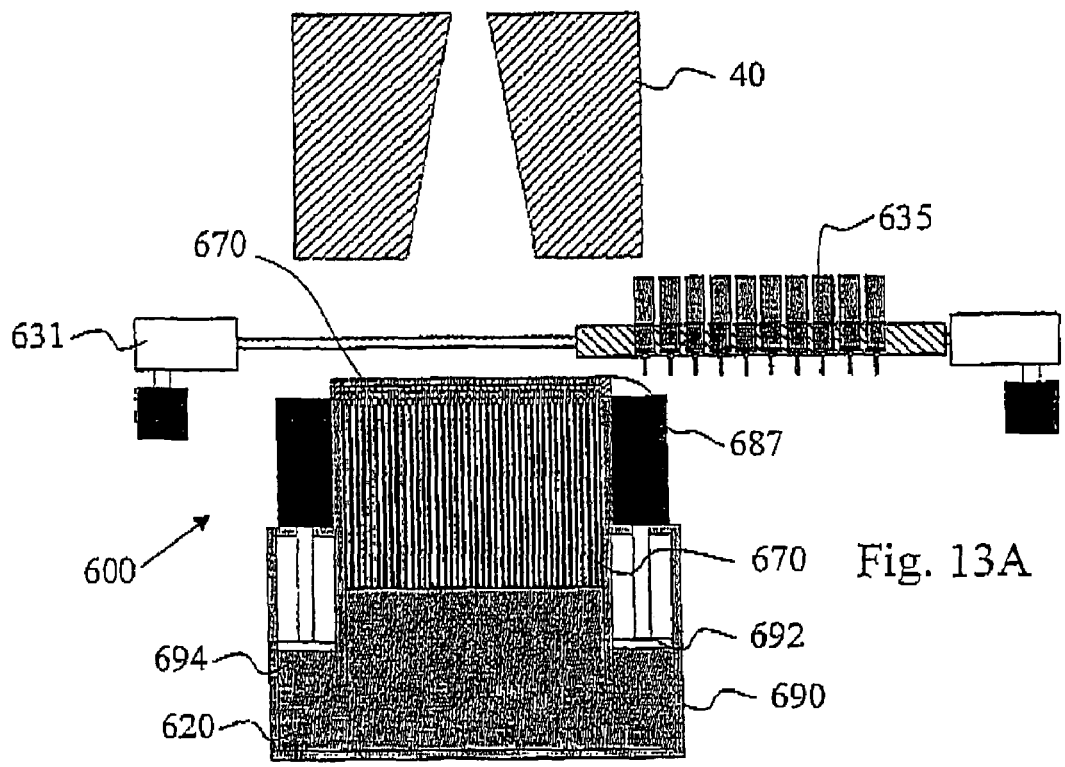

FIGS. 13A to 13E illustrate the operation of the intensity modulator 600 of FIG. 12 in more detail. As can be seen in FIG. 13A, the screw driver system 635 is preferably positioned outside of the intensity modulator 600 and the radiation beam path. In this figure, all low radiation bars 670 are in their uppermost position, i.e. minimal immersion in the radiation attenuating fluid 620. The unit 40 in FIG. 13A represents an optional collimator 40 that can be used for defining and limiting the radiation beam to the extension of the modulator 600.

Figure 13B:
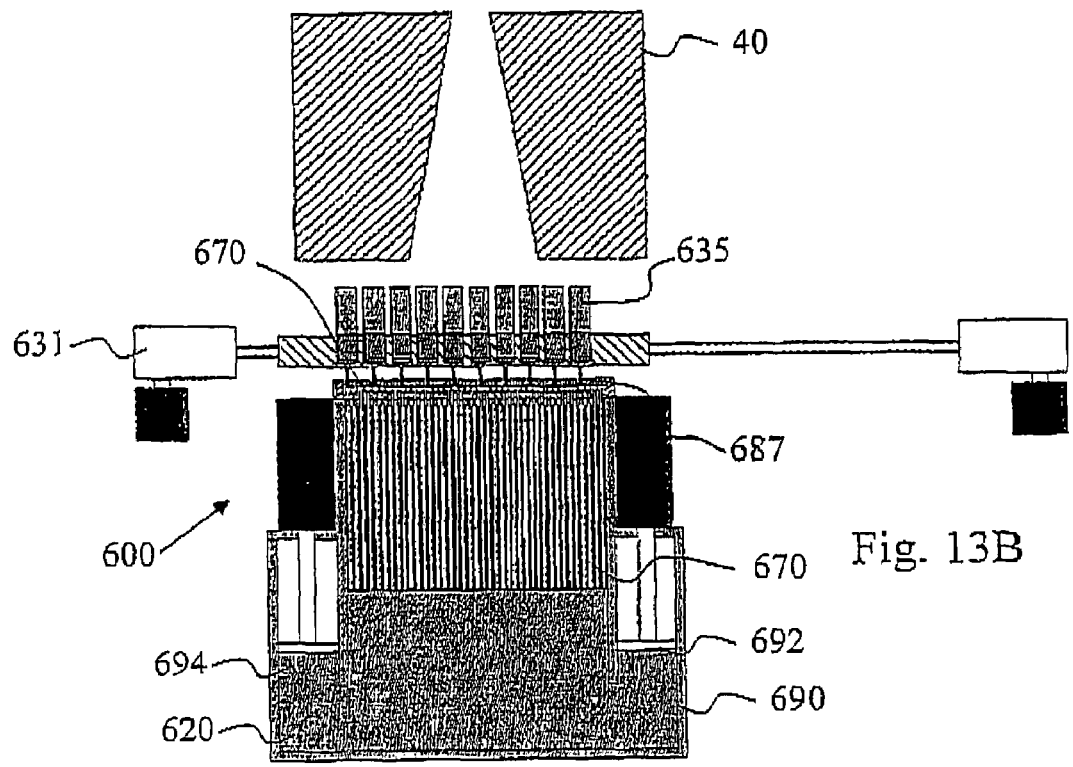

The screw driver system 635 is mounted on a rail system and movable by means of a motor 631. As is illustrated in FIG. 13B, when the modulator profile is to be (dynamically) adjusted, the screw driver system 635 is moved on the rail by the motor 631 from the irradiation position in FIG. 13A to the screwing position in FIG. 13B. Thus, the screw driver system 635 is now placed above the plate 687 with the screw heads and is in position for rotating the screws.

Figure 13C:
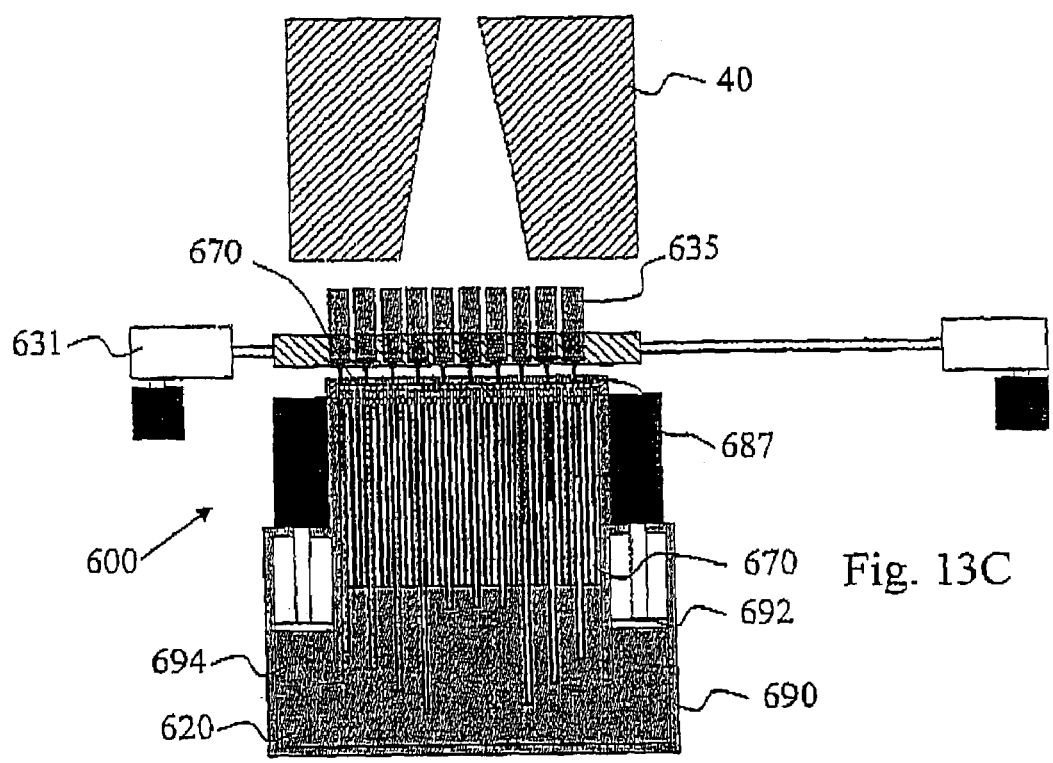
Figure 13D:
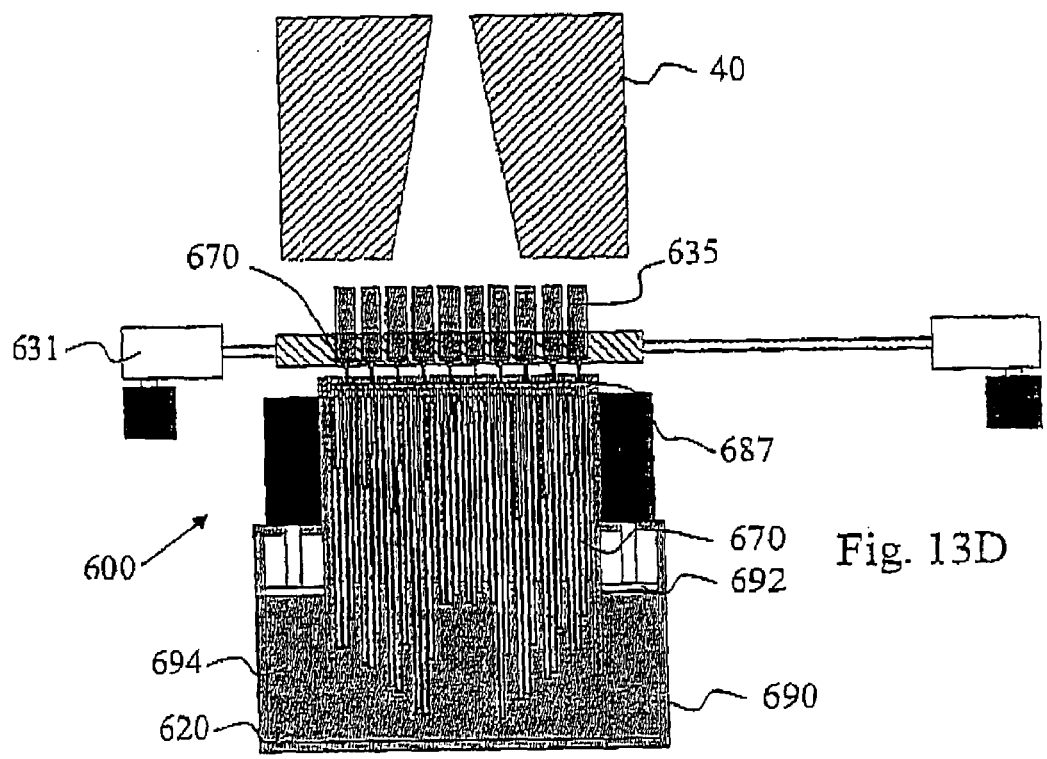

In FIG. 13C, the screw drivers 635 have operated on (rotated) some of the screw heads, with the result that the associated bars 670 become more immersed in the fluid 620. The level of immersion and, thus, the height of the corresponding underlying fluid column depend on how much a screw driver 635 has rotated the screw head associated with the relevant bar 670.

The screw driver system 635 can then be moved step-by-step in order to operate on the different screws in the modulator 600. As can be seen by comparing FIGS. 13C and 13D, as more and more bars 670 become immersed in the fluid 620, the fluid level in the adjacent reservoirs 694 increases, pushing the piston 692 upwards.

Figure 13E:
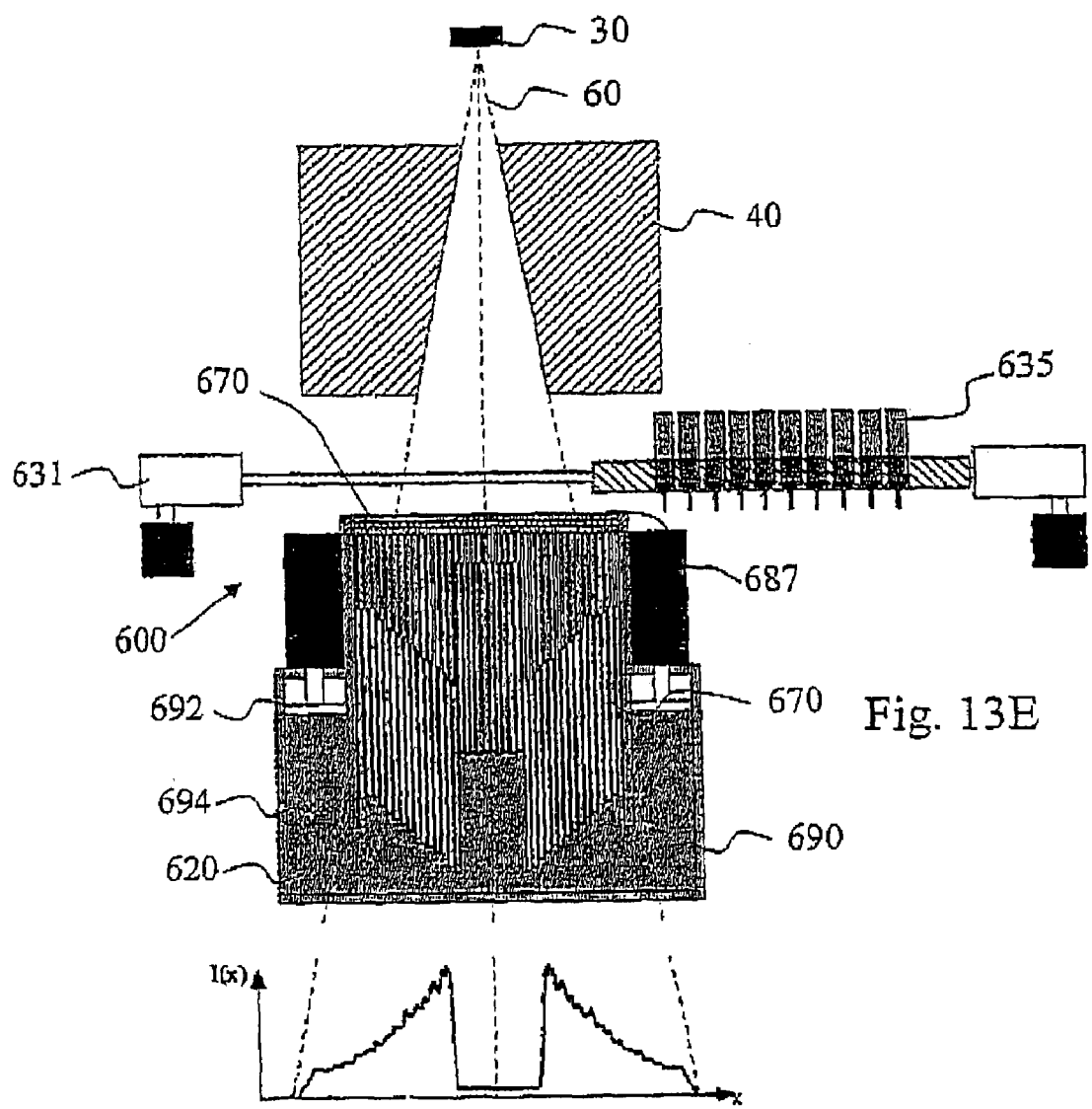

Finally, in FIG. 13E, the screw drivers 635 have adjusted all bars 670 that should be immersed and the target intensity modulating profile is obtained. The screw driver system 635 is then moved by the motor 631 back to the irradiation position away from the radiation beam 60. In this position, the radiation beam 60 from the target 30 will, after passing through the optional collimator 40, become intensity modulated by the fluid profile of the radiation attenuating fluid 620. In the lower part of the figure, the resulting transmission or intensity profile in the plane of the modulator 600 illustrated in FIG. 13E is shown. As can be seen in this diagram, the level of bar immersion and, thus, the fluid column height closely defies the intensity profile of the modulated radiation beam 60.

FIG. 14 is a top view of the core or bundle of bars 670 for the modulator of FIG. 12. This figure illustrates the principle of step-by-step moving the screw drivers 635 of the height adjuster 630 between different bars 670 and screw heads. In this figure there are more bars 670 than screw drivers 635, implying that each screw driver 635 is responsible for and operating on a cell or group 675 of multiple bars 670. In FIG. 14, this bar cell 675 includes 4×4 bars 670. This should, however, merely be seen as an illustrative example and other cell sizes are possible. If the screw driver system includes multiple rows of screw drivers 635, of which one row is illustrated in FIG. 14, and the different rows are aligned with each other, the screw driver system could be regarded as a matrix of screw drivers 635. For such an implementation, each bar cell 675 preferably comprises 2n×m bars, where n, m independently is a positive integer.

The screw drivers 635 are then preferably moved step-by-step along a first row of bars 670 in the cell 675, continuing with step-by-step moving along the second bar row and so on until the screw drivers 635 have been positioned above each bar 670 in their associated cell 675.

FIG. 15 is a three-dimensional view of a possible implementation of the radiation beam modulator 600 of FIG. 12. This figure more clearly illustrates the rail system 631, 633 that allows the system of screw drivers 635 to move to and operate on all screw heads of the modulator 600.

FIG. 16 illustrates a radiation gantry 5 equipped with a radiation beam intensity modulator 1 of the present invention. A beam 10 is directed from a radiation source (not illustrated) via a beam transportation system and deflecting magnets 20 to a target 30. The radiation source, which can be an external electron accelerator or an accelerator that is arranged on the stationary or rotatable part of the gantry 5, typically produces electron beams in the energy range of e.g. 4-50 MeV. The beam transportation system can include different beam processing units, including quadrupoles for focusing the beam 10. The target 30 produces photon beam 60 when the electrons from the accelerator are impinged thereon. In this process, the electrons are converted into bremstrahlung photons. The gantry 5 may further optionally include a flattening filter downstream of the target 30. However, the modulator 1 of the invention works well without any such flattening filter, resulting in a less complex and less expensive radiation system. A collimator 40, e.g. a static or adjustable tungsten collimator, which defines the beam 60 and determines the field size may be arranged upstream or downstream of the modulator 1. Furthermore, when employing the modulator 1 of the invention that utilizes low radiation attenuating bars, a thin peripheral tungsten collimator may be arranged in connection with the modulator 1, preferably downstream thereof, in order to obtain a sharper penumbra. Finally, the gantry 5 can include an optional ion chamber 50 for verification of the accurate dose delivery. This ion chamber 50 could also be used for indirectly verifying the thickness profile of the radiation attenuating fluid in the modulator 1.

The (intensity) modulated radiation beam 60 is then directed onto a target volume (tumor) 75 in a patient 70 lying on a patient couch 90 arranged in connection with the gantry 5. The physical modulator 1 of the invention provides simultaneous whole field irradiation that gives improved photon economy (less beam-on time), which leads to lower accumulated whole-body leakage dose and a substantially shortened treatment time. The fixed fluence of the modulator 1 will result in small dose distribution errors since errors are better averaged during treatment execution.

The gantry 5 can also be equipped with a detector 85, e.g. an electronic portal imaging device, for further verification of the accurate dose delivery. This detector 85 can operate together with or instead of the ion chamber 50 and can also be used for verification of the fluid thickness profile in the modulator 1.

The gantry 5 illustrated in FIG. 16 should merely be seen as an illustrative gantry design, in which the modulator 1 of the invention can be arranged. As a consequence, the modulator 1 can be arranged in other gantry designs and radiation systems.

The intensity modulator of the present invention has been compared to some of the prior art intensity modulated radiation therapy delivery techniques and the results are found in Table 2 below.

TABLE 2

| | Prior art | | | Invention | |
|---|---|---|---|---|---|
| | Physical block | Metal cubes | Reshapable modulator [1] | Bar-based | Capillary-based |
| Max # beams | 3-5 | 3-5 | 5-10 | 5-15 | 5-15 |
| Beam modulation (%) | 100-1 | 100-10 | 100-1.5 | 100-1 | >100-1 |
| Intensity levels | $10^3$ | 10 | $10^3$ | $10^3$ | $10^3$ |
| Spatial resolution (mm) | 2 | 5-10 | 10 | 5 | 5 |
| Setting time (s) | >$10^2$ | >$10^2$ | $10^2$ | 1 | 1 |
| Treatment time ($T_u$) | 1-1.5 | 1-1.5 | 1-1.5 | 0.5-1 | 0.5-1 |

$T_u$ is the standard treatment time for uniform dose delivery to the target volume in one beam direction (1-2 min).

FIG. 17 is a flow diagram over the operation of a radiation beam modulator according to the present invention. The method starts in step S1, where a target transmission profile to use for the radiation beam is defined. This target transmission profiles is determined according to prior art techniques by e.g. employing diagnostic data, which is not described in more detail herein. Based on this target transmission or intensity profile a fluid thickness distribution that will result in the desired target profile is defined. The thickness distribution could e.g. state the fluid column height for each fluid column of the modulator. Alternatively, it could include information of how the modulator should be adjusted in order to obtain the desired modulating profile. Thus, it could state the respective open time of the micro valves or how much fluid the different pumps should pump into or out from the capillaries in the case of a capillary-based modulator. Alternatively, the level of immersion of the bars could be used as adjusting parameter or how much a particular screw head should be rotated or how long a wire motor should be operated.

In a next step S2, the heights of the fluid columns of the radiation modulating fluid are adjusted to obtain the defined modulating profile and fluid thickness distribution that will result in the target transmission profile. In a next optional step S3, the so-adjusted column heights are actively maintained so that the radiation modulation fluid will not move and cause a change in the thickness distribution in the case the modulator is moved or rotated. Finally, in step S4 the irradiation is performed by directing the relevant radiation beam (photon, neutron, electron, ion, positron, $\pi_+$, $\pi_-$, $\pi_0$, light beam, etc.) onto the modulator in order to obtain a modulated (intensity modulated, energy/range modulated, light modulated) beam.

One major advantage of the modulator of the invention is that its modulating profile can be dynamically adjusted in real time during operation without having to move the modulator out from gantry (as for the modulator employing metal cubes and the modulator described in [1]) or replace the modulator (as for fixed transmission blocks). This means that a new target transmission profile can be adjusted, schematically illustrated by the line L1, quickly (part of a second up to a few seconds). This quick column height adjustment can e.g. be performed simultaneously as the gantry and the modulator is rotated to a new irradiation position or angle. This means that the total treatment time will be reduced markedly compared to the prior art solutions.

FIG. 18 is a flow diagram illustrating the adjusting and maintaining steps of FIG. 17 in more detail for the embodiments of the modulator illustrated in FIGS. 1 and 6. The method continues from step S1 in FIG. 17. In a next step S10 it is determined if the pressure ($P_{Lq}$) of the antagonizing pressurizer is larger than the pressure ($P_{Hg}$) exerted by the fluid pressurizer, or vice versa. If $P_{Lq} > P_{Hg}$ the method continues to step S11, where the valves associated with the capillaries for which the level of radiation modulating fluid should be decreased are opened. This results in antagonizing fluid being pushed into the capillaries with open valves and in turn pushing the attenuating fluid partly out from the capillaries and into the fluid reservoir(s). Once the correct fluid column heights have been obtained for these capillaries the valves are closed in step S12.

In a next step S13, the pressure exerted on the radiation attenuating fluid is increased and/or the fluid pressure of the antagonizing fluid is decreased until $P_{Hg} > P_{Lq}$. If any fluid column heights should be increased, the valves associated with these columns and capillaries are opened in step S14, causing radiation attenuating fluid to enter the capillaries and pushing out antagonizing fluid. Once the correct fluid column heights have been obtained for these capillaries the valves are closed in step S15.

If however, $P_{Lq} < P_{Hg}$ as determined in step S10, an increase in the height of the radiation attenuating fluid columns will occur when opening valves in step S16. Once the correct column heights have been obtained the valves are closed in step S17 and the pressure levels are adjusted until $P_{Lq} > P_{Hg}$ in step S18. An opening of the valves in step S19 will result in an influx of antagonizing fluid in the open capillaries and outflow of attenuating fluid. The open valves are then closed in step S15.

The result of these operations is a radiation beam modulating profile that corresponds to the target transmission profile. By employing the antagonizing fluid and the height adjuster, the column heights are actively maintained (locked in position) between two adjustment occasions, thereby preventing any unintentional profile change during irradiation or modulator movement/rotation. The method then continues to step S4 of FIG. 17.

It is anticipated by the present invention that if no column heights need to be increased (decreased) the operation steps S13-S15 or S16-S17 (S11-S12 or S18-S15) can be omitted or skipped.

FIG. 19 is a flow diagram illustrating the adjusting and maintaining steps of FIG. 17 in more detail for the embodiments of the modulator illustrated in FIGS. 7 and 8. The method continues from step S1 in FIG. 17. In a next step S20 pumps are activated in order to pump antagonizing fluid (FIG. 7) or radiation modulating fluid (FIG. 8) into or out from the capillaries. The direction of the pumping and the total pumping time defines the resulting column heights. When the pumps stop, the column heights are locked in position between the antagonizing fluid (that is in turn is lock by the pumps or pressurizer) and the pressurizer or pumps. The method then continues to step S4 in FIG. 17.

FIG. 20 is a flow diagram illustrating the adjusting and maintaining steps of FIG. 17 in more detail for the embodiment of the modulator illustrated in FIG. 12. The method continues from step S1 in FIG. 17. In a next step S30, the screw driver system is moved from the irradiation position outside of the radiation beam area into the screw position aligned to the screw heads. The screw drivers are then activated and screw the screw heads in step S31 in order to immerse/retract the bars further into/from the radiation attenuating fluid. This screwing step can be performed several times if the screw driver system has to be moved between bars (within the bar cell) in order to adjust all the column heights. Once the correct radiation modulating profile is obtained, the screw driver system is moved back to the irradiation position in step S32. The method then continues to step S4 in FIG. 17.

In a further aspect of the present invention there is provided the use of a radiation beam modulator according to the invention for modulating a radiation beam.

It will be understood by a person skilled in the art that various modifications and changes may be made to the present invention without departure from the scope thereof, which is defined by the appended claims.

REFERENCES

[1] Xu T. Shikhaliev PM, Al-Ghazi M and Molloi S. Reshapable physical modulator for intensity modulated radiation therapy, *Medical Physics*, 29(10):2222-2229, 2002
[2] U.S. Pat. No. 5,596,619
[3] Watanabe T and Kuwano H. A microvalve matrix using piezoelectric actuators, *Microsystem Technologies*, 107-111, 1997

The invention claimed is:
1. A radiation beam modulator comprising:
a bath containing a radiation attenuating fluid;
multiple low radiation attenuating bars immersed in said radiation modulating fluid to form an array of multiple fluid columns; and
a height adjuster for adjusting a respective level of immersion of said multiple bars in said radiation modulating fluid thereby to adjust the heights of said multiple fluid columns such that said multiple columns collectively form a radiation beam modulating profile.

2. The modulator according to claim 1, wherein said height adjuster is adapted for individually adjusting said heights of said multiple fluid columns.

3. The modulator according to claim 1, further comprising means for actively maintaining said adjusted heights of said multiple fluid columns.

4. The modulator according to claim 1, wherein said radiation modulating fluid is in liquid form at room temperature.

5. The modulator according to claim 1, wherein said radiation modulating fluid is a radiation attenuating fluid selected from the group consisting of:
mercury;
liquid Rose's metal; and
liquid Wood's metal.

6. The modulator according to claim 1, wherein said multiple bars are made of at least one of:
a low atomic number metal;
beryllium; and
a radiation-resistant plastic.

7. The modulator according to claim 1, wherein each of said multiple bars has a hexagonal cross-section.

8. The modulator according to claim 1, further comprising means for squeezing said multiple bars together to reduce fluid leakage between said multiple bars.

9. The modulator according to claim 1, further comprising multiple wire loops, where a first end of a wire of said multiple wire loops is connected to a first end of a bar of said multiple bars and a second end of said wire is connected to a second opposite end of said bar, said height adjuster comprises a motor system connected to said multiple wire loops and adapted for adjusting said respective level of immersion of said multiple bars in said radiation modulating fluid by rotating said multiple wire loops.

10. The modulator according to claim 1, wherein each of said multiple bars has a blind bore in an end and a nut arranged in connection with said blind bore, said modulator further comprises multiple screws attached, through heads of said screws, to a low radiation attenuation plate arranged in connection with said ends of said multiple bars, said multiple screws running in said blind bores through said nuts, and said height adjuster comprises means for rotating said multiple screws in order to adjust said respective level of immersion of said multiple bars in said radiation modulating fluid.

11. The modulator according to claim 10, wherein said height adjuster comprises a system of screw drivers adapted for individually rotating said multiple screws in order to adjust said respective level of immersion of said multiple bars in said radiation modulating fluid.

12. The modulator according to claim 10, further comprising means for moving said rotating means from at least one screwing position being substantially aligned with said plate to an irradiation position being away from said plate.

13. A radiation gantry comprising:
a radiation source for generating a radiation beam; and
a radiation beam modulator according to claim 1 for modulating said generated radiation beam.

14. A method of operating a radiation beam modulator according to claim 1, said method comprising adjusting heights of multiple fluid columns by adjusting a respective level of immersion of multiple bars in a radiation modulating fluid contained in a bath such that said multiple columns collectively form a radiation beam modulating profile.

15. The method according to claim 14, wherein said adjusting step comprises individually adjusting said heights of said multiple fluid columns.

16. The method according to claim 15, further comprising actively maintaining said adjusted heights of said multiple fluid columns.

* * * * *